United States Patent
Yun et al.

(10) Patent No.: US 9,890,409 B2
(45) Date of Patent: Feb. 13, 2018

(54) COMPOSITION FOR ASTRINGIN PRODUCT

(71) Applicant: INDUSTRY FOUNDATION OF CHONNAM NATIONAL UNIVERSITY, Gwangju (KR)

(72) Inventors: Chul-Ho Yun, Daejeon (KR); Hyung-Sik Kang, Gwangju (KR); Young-Hee Joung, Daejeon (KR); Gun Su Cha, Gwangju (KR)

(73) Assignee: Industry Foundation of Chonnam National University, Gwangju (KR)

(*) Notice: Subject to any disclaimer, the term of this patent is extended or adjusted under 35 U.S.C. 154(b) by 0 days.

(21) Appl. No.: 15/145,679

(22) Filed: May 3, 2016

(65) Prior Publication Data

US 2017/0073720 A1 Mar. 16, 2017

(30) Foreign Application Priority Data

Sep. 10, 2015 (KR) .................. 10-2015-0128399

(51) Int. Cl.
*C12P 17/10* (2006.01)
*C12P 19/46* (2006.01)
*C12N 9/02* (2006.01)

(52) U.S. Cl.
CPC ............ *C12P 19/46* (2013.01); *C12N 9/0071* (2013.01); *C12Y 114/14001* (2013.01)

(58) Field of Classification Search
None
See application file for complete search history.

(56) References Cited

FOREIGN PATENT DOCUMENTS

KR 101048475 B1 7/2011
KR 101348984 B1 1/2014

OTHER PUBLICATIONS

Ngo et al. In the Protein Folding Problem and Tertiary Structure Prediction, 1994, Merz et al. (ed.), Birkhauser, Boston, MA, pp. 433 and 492-495.*

Merrifield, R. B., "Solid Phase Peptide Synthesis. I. The Synthesis of a Tetrapeptide," Journal of the American Chemical Society, vol. 85, No. 14, Jul. 20, 1963, 6 pages.
Omura, T. et al., "The Carbon Monoxide-binding Pigment of Liver Microsomes: II. Solubilization, Purification, and Properties," The Journal of Biological Chemistry, vol. 239, No. 7, Jul. 1964, 8 pages.
Kowalski, D. et al., "Mung Bean Nuclease I. Physical, Chemical, and Catalytic Properties," Biochemistry, vol. 15, No. 20, Oct. 1976, 7 pages.
Yun, C. et al., "Functional Expression of Human Cytochrome P450 Enzymes in *Escherichia coli*," Current Drug Metabolism, vol. 7, No. 4, May 2006, 19 pages.
Kim, D. et al., "Heterologous expression and characterization of wild-type human cytochrome P450 1A2 without conventional N-terminal modification in *Escherichia coli*," Protein Expressions and Purification, vol. 57, No. 2, Feb. 2008, Published Online Oct. 22, 2007, 13 pages.
Kim, D. et al., "Generation of Human Metabolites of 7-Ethoxycoumarin by Bacterial Cytochrome P450 BM3," Drug Metabolism and Disposition, vol. 36, No. 11, Nov. 2008, Published Online Jul. 31, 2008, 5 pages.
Nelson, D., "Cytochrome P450 Homepage," Available Online at http://drnelson.uthsc.edu/CytochromeP450.html, Current Version Oct. 21, 2014, Earlier Version Available as Early as Nov. 2, 2009, 39 pages.
Kang, J. et al,. "Characterization of diverse natural variants of CYP102A1 found within a species of Bacillus megaterium," AMB Express, vol. 1, No. 1, Dec. 2011, Published Online Mar. 28, 2011, 12 pages.
Kang, J. et al., "Chimeric Cytochromes P450 Engineered by Domain Swapping and Random Mutagenesis for Producing Human Metabolites of Drugs," Biotechnology and Bioengineering, vol. 111, No. 7, Jul. 2014, Published Online Feb. 13, 2014, 10 pages.

* cited by examiner

*Primary Examiner* — Richard G Hutson
(74) *Attorney, Agent, or Firm* — McCoy Russell LLP

(57) ABSTRACT

Provided is a composition for producing astringin among metabolites of polydatin, wherein the astringin may be mass-produced by oxidizing the polydatin using a CYP102A1 chimera and mutants thereof as a catalyst, the CYP102A1 chimera being produced by fusing a reductase domain of a wild-type CYP102A1 which is a bacterial cytochrome P450 enzyme, with a heme domain of a CYP102A1 mutant.

2 Claims, 7 Drawing Sheets

FIG. 5

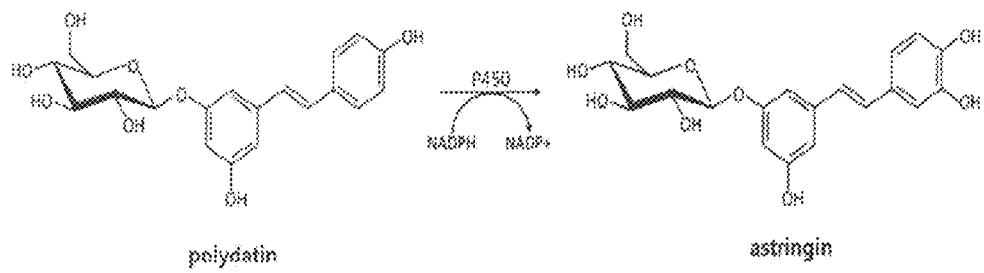

polydatin → astringin

FIG. 6

(1) MDTIKEMPQPKT FGELKNLPLL NTDKPVQALM KIADELGEIF KFEAPGRVTR
(51) YLSSQRLIKE ACDESRFDKN LSQALKFVRD FAGDGLFTSW THEKNWKKAH
(101) NILLPSFSQQ AMKGYHAMMV DIAVQLVQKW ERLNADEHIE VPEDMTRLTL
(151) DTIGLCGFNY RFNSFYRDQP HPFITSMVRA LDEAMNKLQR ANPDDPAYDE
(201) NKRQFQEDIK VMNDLVDKII ADRKASGEQS DDLLTHMLNG KDPETGEPLD
(251) DENIRYQIIT FLIAGHETTS GLLSFALYFL VKNPHVLQKA AEEAARVLVD
(301) PVPSYKQVKQ LKYVGMVLNE ALRLWPTAPA FSLYAKEDTV LGGEYPLEKG
(351) DELMVLIPQL HRDKTIWGDD VEEFRPERFE NPSAIPQHAF KPFGNGQRAC
(401) IGQQFALHEA TLVLGMMLKH FDFEDHTNYE LDIKETLTLK PEGFVVKAKS
(451) KKIPLGGIPS PSTEQSAKKV RKKAENAHNT PLLVLYGSNM GTAEGTARDL
(501) ADIAMSKGFA PQVATLDSHA GNLPREGAVL IVTASYNGHP PDNAKQFVDW
(551) LDQASADEVK GVRYSVFGCG DKNWATTYQK VPAFIDETLA AKGAENIADR
(601) GEADASDDFE GTYEEWREHM WSDVAAYFNL DIENSEDNKS TLSLQFVDSA
(651) ADMPLAKMHG AFSTNVVASK ELQQPGSARS TRHLEIELPK EASYQEGDHL
(701) GVIPRNYEGI VNRVTARFGL DASQQIRLEA EEEKLAHLPL AKTVSVEELL
(751) QYVELQDPVT RTQLRAMAAK TVCPPHKVEL EALLEKQAYK EQVLAKRLTM
(801) LELLEKYPAC EMKFSEFIAL LPSIRPRYYS ISSSPRVDEK QASITVSVVS
(851) GEAWSGYGEY KGIASNYLAE LQEGDTITCF ISTPQSEFTL PKDPETPLIM
(901) VGPGTGVAPF RGFVQARKQL KEQGQSLGEA HLYFGCRSPH EDYLYQEELE
(951) NAQSEGIITL HTAFSRMPNQ PKTVYVQHVME QDGKKLIELL DQGAHFYICG
(1001) DGSQMAPAVE ATLMKSYADV HQVSEADARL WLQQLEEKGR YAKDVWAG

MTIKEMPQPK TFGELKNLPL LNTDKPVQAL MKJADELGEI FKFEAPGLVT RYLSSQRLIKEACDESRFDK
NLSQALKFVR DFAGDGIVTS WTHEKNWKKA HNILLPSFSQ QAMKGYHAMM VDIAVQLVQK
WERLNADEHI EVPGDMTRLT LDTIGLCGFN YRFNSFYRDQ PHPFITSMVR ALDEAMNKQQ
RANPDDPAYD ENKRQFQEDI KVMNDLVDKI IADRKASGEQ SDDLLTHMLNGKDPETGEPL DDENIRYQII
TFLIAGHVTT SGLLSFALYF LVKNPHVLQK AAEEAARVLV DPVPSYKQVK QLKYVGMVLN EALRLWPTAP
AFSLYAKEDT VLGGEYPLEK GDELMVLIPQ LHRDKTIWGD DVEEFRPERF ENPSAIPQHA FKPFGNGQRA
CIGQQFALHE ATLVLGMMLK HFDFEDHTNY ELDIKETLTL KPEGFVVKAK SKKIPLGGIP SPSTEQSAKK
VRKKVENAHN TPLLVLYGSN MGTAEGTARD LADIAMSKGF APQVATLDSH AGNLPREGAV LIVTASYNGH
PPDNAKQFVD WLDQASADDV KGVRYSVFGC GDKNWATTYQ KVPAFIDETL AAKGAENIAD
RGEADASDDF EGTYEEWREH MWSDVAAYFN LDIENSEDNK STLSLQFVDS AADMPLAKMH
GAFSANVVAS KELQQLGSER STRHLEIALP KEASYQEGDH LGVIPRNYEG IVNRVTARFG LDASQQIRLE
AEEEKLAHLP LGKTVSVEEL LQYVELQDPV TRTQLRAMAA KTVCPPHKVE LEALLEKQAY KEQVLAKRLT
MLELLEKYPA CEMEFSEFIA LLPSISPRYY SISSSPHVDE KQASITVSVV SGEAWSGYGE YKGIASNYLA
NLQEGDTITC FVSTPQSGFT LPKDSETPLI MVGPGTGVAP FRGFVQARKQ LKEQGQSLGE AHLYFGCRSP
HEDYLYQEEL ENAQNEGIT LHTAFSRVPN QPKTYVQHVM ERDGKKLIEL LDQGAHFYIC GDGSQMAPDV
EATLMKSYAD VVEVSEADAR LWLQQLEEKG RYAKDVWAG

* Numbering of amino acid sequences starts from threonine (T) which is a second amino acid, rather than methionine (M).

FIG. 9

COMPOSITION FOR ASTRINGIN PRODUCT

CROSS-REFERENCE TO RELATED APPLICATIONS

This application claims priority under 35 U.S.C. § 119 to Korean Patent Application No. 10-2015-0128399, filed on Sep. 10, 2015, in the Korean Intellectual Property Office, the disclosure of which is incorporated herein by reference in its entirety.

INCORPORATION BY REFERENCE OF ELECTRONICALLY SUBMITTED MATERIAL

Incorporated by reference in its entirety herein is a computer-readable nucleotide and amino acid sequence listing submitted herewith and identified as follows: 28,120 bytes ASCII (Text) file named "Substitute_Sequence_Listing_PLS16309," created Sep. 9, 2016.

TECHNICAL FIELD

The following disclosure relates to a novel composition including a bacterial cytochrome P450 chimera for producing astringin or mutants thereof, a kit and a method for producing astringin using the same.

BACKGROUND

Polydatin which is known as stilbenoid-based drug has effects on anti-oxidant, anti-aging, anti-virus, neuroprotective action, and anti-inflammatory action. Polydatin is a stilbenoid glucoside, and is a derivative of resveratrol, and the stilbenoid-based drug such as polydatin is known to be metabolized by CYP1A2 and CYP1B1 which are cytochrome P450 enzymes present in human liver. However, metabolic pathways and metabolites of polydatin have not been specifically known so far.

The cytochrome P450 enzyme is present throughout all living organisms including archaea, bacteria, fungi, plants, animals, and human, and corresponds to a large family consisting of enzymes serving as catalysts promoting various oxidation reaction (http://drnelson.uthsc.edu/CytochromeP450.html).

P450 is significantly various in view of kinds, and may function as catalysts for a wide range of substrates, thereby having a potential for being effectively useful as a biological catalyst in production of fine chemicals such as pharmaceutical products. However, despite the potential usefulness, P450 enzymes have problems in being used as a biological catalyst due to low stability, catalytic activity, and availability.

P450 is capable of being used to synthesize drug metabolites, in particular, chiral metabolites by a simple, highly efficient, and environment-friendly method, wherein the synthesis of the chiral metabolites is not suitably performed by chemical methods, but needs to use an enzyme. If the drug acts as a prodrug, the drug is converted to a biologically active metabolite by P450s of the human liver when the drug metabolizes after administration. Here, in order to conduct research into drug efficacy, toxic, pharmacokinetics, and the like, of active metabolites produced from the prodrugs, a large amount of pure metabolites are needed. Further, when the metabolites themselves have biological activities, direct administration of the metabolites in vivo may provide big benefits, such that technique for mass-producing the metabolites is significantly important.

However, there are a lot of problems in chemically synthesizing pure metabolites. In addition, as an alternative thereof, a human P450 enzyme is used, but it is technically almost impossible to directly separate only P450 enzymes from a human sample. Further, even in the case of animal-derived P450, it is difficult to perform pure-separation, and enzyme activity is also low. In order to solve the problems, there was an attempt to produce metabolites using human P450 which is heterologously expressed in $E.\ coli$ or insect cells, but the attempt has problems such as limited stability, a slow response rate, high cost and low productivity.

As another method, there was a method using bacterial P450 enzymes which are engineered to have catalytic activity, and a possibility that P450 enzymes capable of functioning on various substrates are appropriately usable for producing biotechnological metabolites by using the engineered enzymes has been reported.

Therefore, the present inventors conducted research into pathways and metabolites of polydatin, found bacterial P450 chimera enzyme capable of selectively producing specific metabolites among the metabolites of polydatin, and completed the present invention.

RELATED ART DOCUMENT (Patent Document 1) Korean Patent No. 1348984

SUMMARY

An embodiment of the present invention is directed to providing a novel composition including a bacteria P450 chimeric enzyme capable of mass-producing astringin among metabolites of polydatin that is not capable of being mass-produced by chemical synthesis, and mutants thereof.

In one general aspect, there is provided a composition for producing astringin including at least one enzyme of the group consisting of mutants of CYP102A1 chimera and the CYP102A1 chimera, and producing astringin by oxidizing polydatin, wherein the CYP102A1 chimera is R47L/F81I/F87V/E143G/L188Q/E267V/A475V/E559D/T665A/P676L/A679E/E688A/A742G/K814E/R826S/R837H/E871N/I882V/E888G/P895S/S955N/M968V/Q982R/A1009D/H1022Y/Q1023E of a CYP102A1 mutant, the CYP102A1 mutant is R47L/F81I/F87V/E143G/L188Q/E267V of a wild-type CYP102A1, and the mutant of CYP102A1 chimera is at least one selected from the group consisting of F11L/R47L/F81I/F87V/Q110P/E143G/L188Q/R190Q/E267V, R47L/F81I/F87V/L103F/D136G/E143G/N159S/L188Q/E267V, and R47L/F81I/F87V/M112T/E143G/L188Q/E267V/M417T of the CYP102A1 chimera.

In another general aspect, there is provided a method for producing astringin including: reacting at least one enzyme of the group consisting of mutants of CYP102A1 chimera and the CYP102A1 chimera, using polydatin as a substrate, wherein the CYP102A1 chimera is R47L/F81I/F87V/E143G/L188Q/E267V/A475V/E559D/T665A/P676L/A679E/E688A/A742G/K814E/R826S/R837H/E871N11882V/E888G/P895S/S955N/M968V/Q982R/A1009D/H1022Y/Q1023E of a CYP102A1 mutant, the CYP102A1 mutant is R47L/F81I/F87V/E143G/L188Q/E267V of a wild-type CYP102A1, and the mutant of CYP102A1 chimera is at least one selected from the group consisting of F11L/R47L/F81I/F87V/Q110P/E143G/L188Q/R190Q/E267V, R47L/F81I/F87V/L103F/D136G/

E143G/N159S/L188Q/E267V, and R47L/F81I/F87V/ M112T/E143G/L188Q/E267V/M417T of the CYP102A1 chimera.

BRIEF DESCRIPTION OF THE DRAWINGS

FIG. 5 shows production of astringin by oxidation of polydatin.

FIG. 6 shows amino acid sequence of wild-type bacteria CYP102A1, and numbering of the amino acid sequences starts from threonine (T) which is a second amino acid, rather than methionine (M).

FIG. 7 shows base sequence of CYP102A1 chimera (M16V3), SEQ ID NO: 17.

FIG. 8 shows amino acid sequence of CYP102A1 chimera (M16V3), SEQ ID NO:

Figure 9:
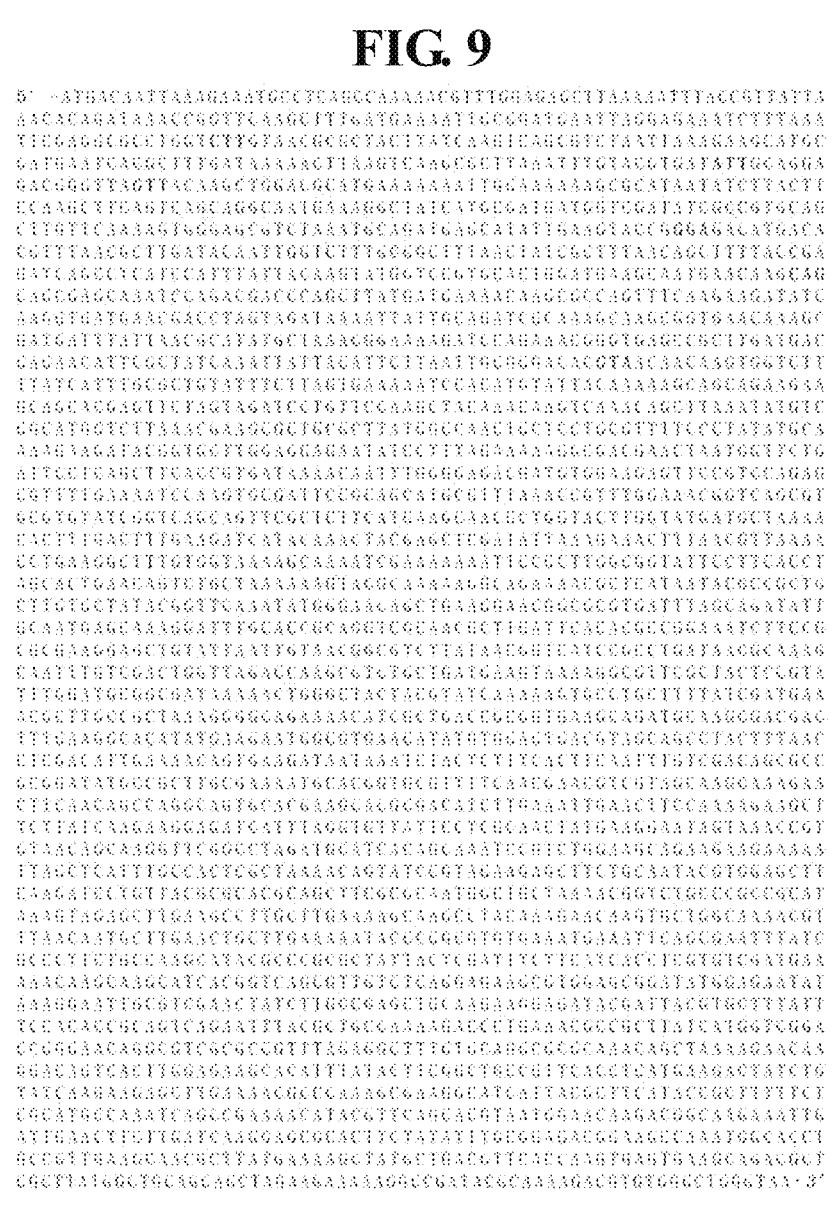

FIG. 9 shows base sequence of a mutant #16 of a wild-type CYP102A1 SEQ ID NO: 19.

DETAILED DESCRIPTION OF EMBODIMENTS

Figure 1:
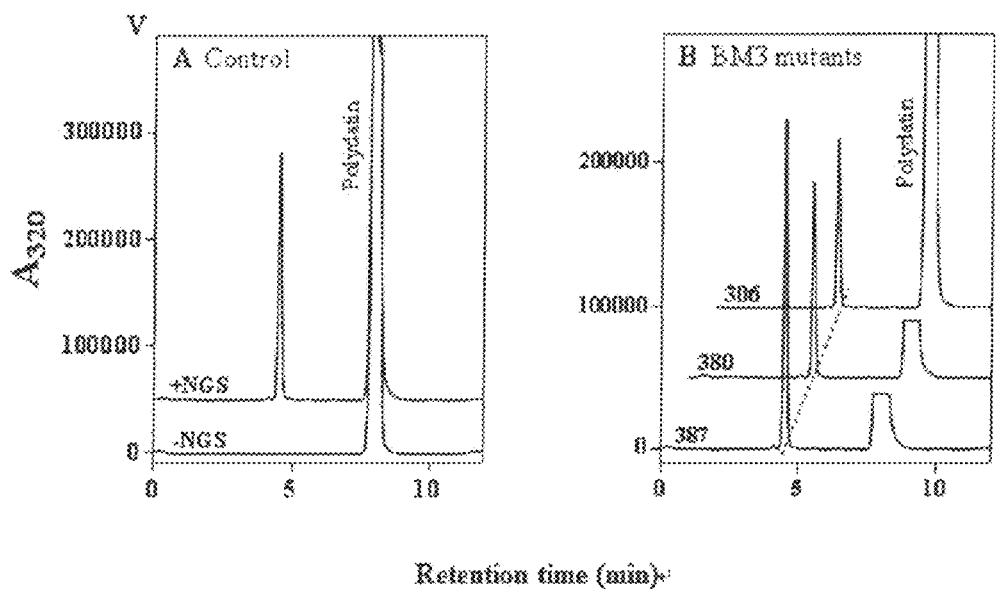
In FIG. 1, (A) shows comparison between peak of a new metabolite with NADPH-generating system and peak of a metabolite without the NADPH-generating system, and (B) shows astringin which is a 3'-OH hydroxylated product by mutants of CYP102A1 chimera.

Hereinafter, the present invention is described in detail. Unless indicated otherwise in the specification, it is to be understood that all the technical terms used in the specification are construed as meaning as those that are generally understood by those skilled in the art. Further, in the drawings for describing the present invention, portions will be omitted so as not to obscure the gist of the present invention, and may be exaggerated in the range in which the gist of the present invention is not obscured.

The present invention provides a novel composition including a bacterial cytochrome P450 chimera enzyme capable of producing astringin which is 3'-hydroxypolydatin among metabolites of polydatin, and mutants thereof.

The present invention provides a method for producing astringin from polydatin by using wild-type CYP102A1 which is bacterial cytochrome P450 BM3 as a bacterial cytochrome P450 chimeric enzyme, a CYP102A1 chimera fused from a mutant thereof or a mutant of CYP102A1 chimera as a catalyst, a composition thereof, and a kit including the same.

In the present invention, the chimera may include at least two different binding domains. The two binding domains may be derived from different wild-type proteins or mutants, and the two binding domains may be derived from the same wild-type proteins or mutants.

The present invention provides a composition for producing astringin including at least one enzyme of the group consisting of mutants of CYP102A1 chimera and the CYP102A1 chimera, and producing astringin by oxidizing polydatin, wherein the CYP102A1 chimera is R47L/F81I/ F87V/E143G/L188Q/E267V/A475V/E559D/T665A/ P676L/A679E/E688A/A742G/K814E/R826S/R837H/ E871N11882V/E888G/P895S/S955N/M968V/Q982R/ A1009D/H1022Y/Q1023E of a CYP102A1 mutant, the CYP102A1 mutant is R47L/F81I/F87V/E143G/L188Q/ E267V of a wild-type CYP102A1, and the mutant of CYP102A1 chimera is at least one selected from the group consisting of F11L/R47L/F81I/F87V/Q110P/E143G/ L188Q/R190Q/E267V, R47L/F81I/F87V/L103F/D136G/ E143G/N159S/L188Q/E267V, and R47L/F81I/F87V/ M112T/E143G/L188Q/E267V/M417T of the CYP102A1 chimera.

In the present invention, the CYP102A1 chimera may be produced by fusing a heme domain of wild-type CYP102A1 mutant with a reductase domain of a natural variant of the wild-type CYP102A1, and may be positioned with a different arrangement from proteins of the wild-type CYP102A1 mutants.

The natural variants in the present invention mean mutants which are confirmed to be present in nature by analyzing base sequence of CYP102A1 gene of *bacillus* sp. that is collected in the nature and deposited, in addition to CYP102A1 which is previously known in the art.

In the present invention, the CYP102A1 chimera was selected from mutants having a large catalytic activity to substrates among the mutants obtained by mass-expressing the wild-type CYP102A1 and site-directed mutants thereof in *E. coli*, and may be produced by fusing the heme domain of the selected CYP102A1 mutant with the reductase domain of the natural variant of the wild-type CYP102A1. Further, the mutant of CYP102A1 chimera may be selected from mutants having a large catalytic activity by mass-expressing the site-directed mutants of the produced chimera in *E. coli*.

In the present invention, the CYP102A1 mutants have sequences changed by natural or artificial substitution, deletion, addition and/or insertion in wild-type CYP102A1 protein amino acids. Preferably, the amino acids to be substituted may be substituted to have similar characteristics to amino acids that will be substituted. For example, alanine, valine, leucine, isoleucine, proline, methionine, phenylalanine and tryptophan are classified into non-polar amino acids, and may have similar characteristics to be substituted with each other. Amino acids having no charges include glycine, serine, threonine, cysteine, tyrosine, asparagine, and glutamine, which may be substituted with each other. Further, acidic amino acids include aspartic acid and glutamic acid, which may be substituted with each other, and basic amino acids include lysine, arginine, and histidine, which may be substituted with each other.

The CYP102A1 mutants may be produced by mutagenesis methods known in the art. For example, a deletion-mutagenesis method (Kowalski D et al., J. BioChem., 15, 4457 reference), PCT method, Kunkel method, a site-directed mutagenesis method, DNA shuffling, a staggered extension process (StEP), an error-prone PCR method may be used.

In the present invention, the CYP102A1 mutant may include polypeptide including amino acid sequences having at least 50%, preferably 70%, more preferably 90% identity to the wild-type CYP102A1 amino acid sequence consisting of SEQ ID NO: 16.

According to an exemplary embodiment of the present invention, the CYP102A 1 mutant may include at least one substitution selected from the group consisting of an arginine (R) (47th amino acid of the wild-type CYP102A1) to leucine (L) substitution, a phenylalanine (F) (81th amino acid of the wild-type CYP102A1) to isoleucine (I) substitution, a phenylalanine (F) (87th amino acid of the wild-type CYP102A1) to valine (V) substitution, a glutamic acid (E) (143th amino acid) to glycine (G) substitution, a leucine (L) (188th amino acid) to glutamine (Q) substitution, and a glutamic acid (E) (267th amino acid) to valine (V) substitution.

In the present invention, the preferable CYP102A1 mutant may be R47L/F81I/F87V/E143G/L188Q/E267V of the wild-type CYP102A1, but the present invention is not limited thereto.

In the present invention, the CYP102A1 mutant may be represented by an amino acid prior to the mutation, a position of the amino acid in SEQ ID NO: 16, and an amino acid which is substituted due to the mutation. For example, F87A means a CYP102A1 mutant in which phenylalanine (F) (87th amino acid of SEQ ID NO: 16 which is the amino acid sequence of the wild-type CYP102A1) is substituted with valine (V) by natural or artificial mutagenesis. When the amino acid substituted by the mutation in the mutant is at least one, the amino acid may be represented by '/'. For example, F87A/A264G means a mutant of CYP102A1 in which phenylalanine (F) (87th amino acid of SEQ ID NO: 16) is substituted with valine (V), and alanine (A) (264th amino acid of SEQ ID NO: 16) is substituted with glycine (G). The above-described representation of the mutants may be used to represent the mutation of CYP102A1 chimera or the mutants of CYP102A1 chimera in the present invention.

In the present invention, the CYP102A1 chimera may be produced by fusing the heme domain of the CYP102A 1 mutant with the reductase domain of the natural variant of the wild-type CYP102A1.

According to an exemplary embodiment of the present invention, the CYP102A1 chimera may include sequences changed by at least one substitution selected from the group consisting of an alanine (A) (475th amino acid) to valine (V) substitution, a glutamic acid (E) (559th amino acid) to aspartic acid (D) substitution, a threonine (T) (665th amino acid) to alanine (A) substitution, a proline (P) (676th amino acid) to leucine (L) substitution, an alanine (A) (679th amino acid) to glutamic acid (E) substitution, a glutamic acid (E) (688th amino acid) to alanine (A) substitution, an alanine (A) (742th amino acid) to glycine (G) substitution, a lysine (K) (814th amino acid) to glutamic acid (E) substitution, an arginine (R) (826th amino acid) to serine (S) substitution, an arginine (R) (837th amino acid) to histidine (H) substitution, a glutamic acid (E) (871th amino acid) to asparagine (N) substitution, an isoleucine (I) (882th amino acid) to valine (V) substitution, a glutamic acid (E) (888th amino acid) to glycine (G) substitution, a proline (P) (895th amino acid) to serine (S) substitution, a serine (S) (955th amino acid) to asparagine (N) substitution, a methionine (M) (968th amino acid) to valine (V), a glutamine (Q) (982th amino acid) to arginine (R) substitution, an alanine (A) (1009th amino acid) to aspartic acid (D) substitution, a histidine (H) (1022th amino acid) to tyrosine (Y) substitution, and a glutamine (Q) (1023th amino acid) to glutamic acid (E) substitution, in the reductase domain of the CYP102A mutant.

In the present invention, the preferable CYP102A1 chimera may be R47L/F81 I/F87V/E143G/L188Q/E267V/ A475V/E559D/T665A/P676L/A679E/E688A/A742G/ K814E/R826S/R837H/E871N/I882V/E888G/P895S/ S955N/M968V/Q982R/A1009D/H1022Y/Q1023E of the CYP102A1 mutant, but the present invention is not limited thereto.

In the present invention, the mutant of CYP102A1 chimera may be selected from mutants induced from the CYP102A1 chimera.

According to an exemplary embodiment of the present invention, the mutant of CYP102A1 chimera may include sequences changed by at least one substitution selected from the group consisting of a phenylalanine (f) (11th amino acid of CYP102A1 chimera) to leucine (L) substitution, an arginine (R) (47th amino acid) to leucine (L) substitution, a phenylalanine (F) (81th amino acid) to isoleucine (I) substitution, a phenylalanine (F) (87th amino acid) to valine (V) substitution, a leucine (L) (103th amino acid) to phenylalanine (F) substitution, a glutamine (Q) (110th amino acid) to proline (P) substitution, a methionine (M) (112th amino acid) to threonine (T) substitution, an aspartic acid (D) (136th amino acid) to glycine (G) substitution, glutamic acid (E) (143th amino acid) to glycine (G) substitution, asparagine (N) (159th amino acid) to serine (S) substitution, leucine (L) (188th amino acid) to glutamine (Q) substitution, an arginine (R) (190th amino acid) to glutamine (Q) substitution, a glutamic acid (E) (267th amino acid) to valine (V) substitution, and a methionine (M) (417th amino acid) to threonine (T) substitution.

In the present invention, the mutant of the preferable CYP102A1 chimera may be selected from the group consisting of F11L/R47L/F81I/F87V/Q110P/E143G/L188Q/ R190Q/E267V, R47L/F81I/F87V/L103F/D136G/E143G/ N159S/L188Q/E267V, and R47L/F81I/F87V/M112T/ E143G/L188Q/E267V/M417T of the CYP102A1 chimera, but the present invention is not limited thereto.

Figure 4:
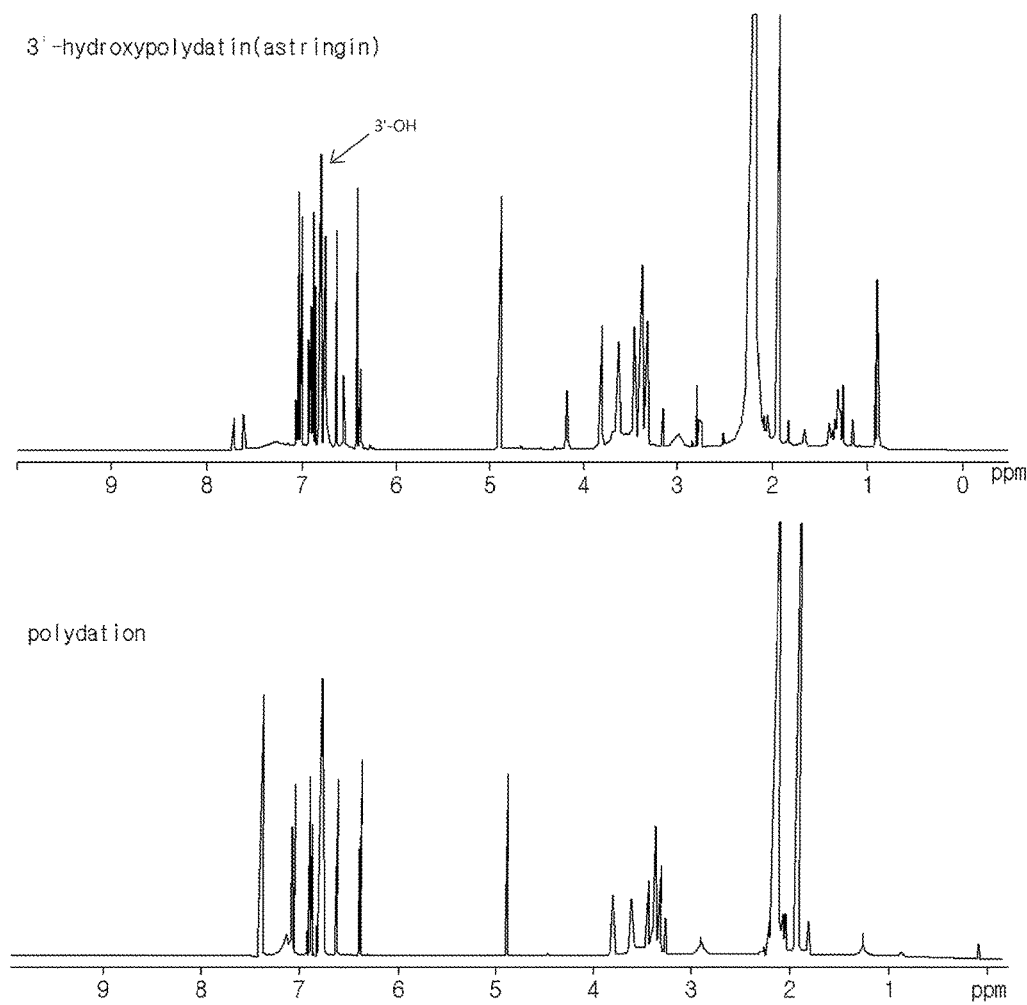
FIG. 4 shows results of the obtained products by NMR analysis, confirming that the obtained products are astringin (A) which is 3'-hydroylated product and polydatin (B).

According to an exemplary embodiment of the present invention, the astringin which is 3'-hydroxypolydatin may be produced from the polydatin by at least one enzyme of the group consisting of the mutants of CYP102A1 chimera and the CYP102A1 chimera, which may be confirmed by methods such as HPLC (FIG. 1), LC-MS spectrum (FIG. 2), and NMR spectra (FIG. 4). In addition, it may be appreciated that the mutants of the CYP102A1 chimera have higher molecular catalytic activity than the CYP102A1 chimera.

In the present invention, the wild-type CYP102A1, the CYP102A1 mutant, the CYP102A1 chimera and the mutant of CYP102A1 chimera may be produced by methods known in the art. For example, the production methods may include genetic engineering technique, peptide synthesis using solid-phase technique (Merrifield, J. Am. Chem. Soc., 85: 2149-2154 (1963)), a method of cutting the enzymes of the present invention by an appropriate peptidase, and the like.

In the present invention, the enzymes may be produced as natural protein, and may be produced by a recombinant method including culturing and recovering cells transformed with DNA encoding the wild-type CYP102A1, the CYP102A1 mutant, the CYP102A1 chimera, and the mutants of CYP102A1 chimera. Specifically, the enzymes of the present invention may be produced by inserting nucleic acid molecules encoding the enzymes of the present invention into a suitable expression vector, delivering the expression vector to an appropriate cell to form a transformant, culturing the transformant, and purifying the enzymes expressed by the transformant.

In the present invention, the vector may be a plasmid, cosmid, virus particle, or phage.

Example of a host cell cloning or expressing DNA in the vector may include a prokaryotic cell, yeast and a higher eukaryotic cell. Culture conditions such as medium, temperature, pH, and the like, may be appropriately selected without undue experiments in the art to which the invention pertains. For example, principles, protocols, techniques, and the like, for maximizing productivity of cell culture may be used with reference to Mammalian Cell Biotechnology: A Practical Approach, M. Butler, ed. (IRL Press, 1991) among a number of known methods.

In the present invention, expression and cloning vectors may generally include promoters operably linked to a nucleic acid sequence encoding the wild-type CYP102A1 inducing mRNA synthesis, the CYP102A1 mutant, the CYP102A1 chimera and the mutants of CYP102A1 chimera. Various promoters recognized by the host cell are known. Examples of the promoter appropriate for being used in prokaryotic hosts include β-lactamase and lactose promoter system, alkaline phosphatase, a tryptophan promoter system, and a hybrid promoter, for example, a tac promoter. A promoter used in a bacterial system may include Shine-Dalgarno (S.D.) sequence operably linked to DNA encoding SISP-1. Examples of the promoter sequence appropriate for being used in a yeast host may include 3-phosphoglycerate kinase or other glycolytic enzymes.

The present invention provides a method for producing astringin including: reacting at least one enzyme of the group consisting of mutants of CYP102A1 chimera and the CYP102A1 chimera, using polydatin as a substrate.

The present invention provides the method for producing astringin including: reacting at least one enzyme of the group consisting of mutants of CYP102A1 chimera and the CYP102A1 chimera, using polydatin as a substrate, wherein the CYP102A1 chimera is R47L/F81I/F87V/E143G/L188Q/E267V/A475V/E559D/T665A/P676L/A679E/E688A/A742G/K814E/R826S/R837H/E871N/I882V/E888G/P895S/S955N/M968V/Q982R/A1009D/H1022Y/Q1023E of a CYP102A1 mutant, the CYP102A1 mutant is R47L/F81I/F87V/E143G/L188Q/E267V of a wild-type CYP102A1, and the mutant of CYP102A1 chimera is at least one selected from the group consisting of F11L/R47L/F81I/F87V/Q110P/E143G/L188Q/R190Q/E267V, R47L/F81I/F87V/L103F/D136G/E143G/N159S/L188Q/E267V, and R47L/F81I/F87V/M112T/E143G/L188Q/E267V/M417T of the CYP102A1 chimera.

The method for producing astringin in the present invention may further include: an NADPH-generating system.

The NADPH-generating system in the present invention may be the same as known in the art. Preferably, glucose 6-phosphate, NADPH- and yeast glucose 6-phosphate dehydrogenase may be used, but the present invention is not limited thereto.

The present invention may provide a kit for producing astringin including at least one enzyme of the group consisting of mutants of CYP102A1 chimera and the CYP102A1 chimera, and an NADPH-generating system.

The present invention may provide the kit for producing astringin including at least one enzyme of the group consisting of mutants of CYP102A1 chimera and the CYP102A1 chimera, and an NADPH-generating system, and producing astringin by oxidizing polydatin, wherein the CYP102A1 chimera is R47L/F81I/F87V/E143G/L188Q/E267V/A475V/E559D/T665A/P676L/A679E/E688A/A742G/K814E/R826S/R837H/E871N/I882V/E888G/P895S/S955N/M968V/Q982R/A1009D/H1022Y/Q1023E of a CYP102A1 mutant, the CYP102A1 mutant is R47L/F81I/F87V/E143G/L188Q/E267V of a wild-type CYP102A1, and the mutant of CYP102A1 chimera is at least one selected from the group consisting of F11L/R47L/F81I/F87V/Q110P/E143G/L188Q/R190Q/E267V, R47L/F81I/F87V/L103F/D136G/E143G/N159S/L188Q/E267V, and R47L/F81I/F87V/M112T/E143G/L188Q/E267V/M417T of the CYP102A1 chimera.

The kit according to the present invention may further include reagents required for performing the reaction for producing the astringin.

With the composition for producing the astringin, the kit, and the production method according to the present invention, the astringin which is the metabolite of polydatin that is not capable of being chemically synthesized may be economically mass-produced at high yield, thereby being effectively usable for various research and drug development.

Hereinafter, the present invention is specifically described by Examples. The following Examples are provided as an example for practicing the present invention, and therefore, the present invention is not limited to the following Examples.

EXAMPLE 1

Construction of P450 BM3 Mutant by Site-Directed Mutagenesis

Seventeen (17) CYP102A1 site-directed mutants were constructed by the same method as a method described in research paper (see Generation of Human Metabolites of 7-Ethoxycoumarin by Bacterial Cytochrome P450 BM3. Drug Metabolism and Disposition 36(11):2166-2170. Page 2 (Page 2167), Materials and Methods, Construction of BM3 Mutants by Site-directed Mutagenesis, written by Kim D. H., Kim K. H., Kim D. H., Liu K. H., Jung H. C., Pan J. G., and Yun C. H. (2008)). Primers used for introducing BanHI/SacI restriction sites and PCR primers (XENOTECH, Korea) for inducing mutations were shown in Table 1. Codons for amino acid substitution were expressed in italics and underlines. The genes encoding CYP102A1 mutants were amplified from pCWBM3 by PCR using primers designed for facilitate cloning into expression vector pCWori (obtained by Dr. F. W. Dahlquist, University of California, Santa Barbara, Calif.) or pSE420 (Invitrogen) (see Chimeric Cytochromes P450 Engineered by Domain Swapping and Random Mutagenesis for Producing Human Metabolites of Drugs, Biotechnology and Bioengineering 111(7):1313-1322. Page 1315, written by Kang J. Y., Ryu S. H., Park S. H., Cha G. S., Kim D. H., Kim K. H., Hong A. W., Ahn T., Pan J. G., Joung Y. H., Kang H. S., and Yun C. H. (2014)). Oligonucleotide assembly was performed by using the primers shown in Table 1. The amplified genes were cloned into the BamHI/SacI restriction sites of PCWBM3 BamHI/SacI vector. The plasmids were transformed into *Escherichia coli* DH5α F'-IQ (Invitrogen) and were also used to express the CYP102A1 mutant protein. After mutagenesis, the presence of the desired mutations was confirmed by DNA sequencing (XENOTECH, Korea). The wild-type CYP102A1 amino acid sequence (SEQ ID NO: 16) used for the construction of P450 BM3 mutant was the same as being shown in FIG. 6. In accordance with the convention, the first amino acid, methionine (M), was not included in the amino acid sequence, and threonine (T) was calculated as the first amino acid.

| name | sequence |
|---|---|
| BamHi forward (SEQ ID NO: 1) | 5'-AGC GGA TCC ATG ACA ATT AAA GAA ATG CCT C-3' |
| SacI (SEQ ID NO: 2) | 5'-ATC GAG CTC GTA GTT TGT AT-3' |
| R47L (SEQ ID NO: 3) | 5'-GCG CCT GGT CTG GTA ACG CG-3' |
| Y51F (SEQ ID NO: 4) | 5'-GTA ACG CGC TTC TTA TCA AGT-3' |
| E64G (SEQ ID NO: 5) | 5'-GCA TGC GAT GGC TCA CGC TTT-3' |
| a74G (SEQ ID NO: 6) | 5'-TA AGT CAA GGC CTT AAA TTT GTA CG-3' |
| F81I (SEQ ID NO: 7) | 5'-GTA CGT GAT ATT GCA GGA GAC-3' |
| L86I (SEQ ID NO: 8) | 5'-GGA GAC GGG ATT TTT ACA AGC T-3' |
| F87A (SEQ ID NO: 9) | 5'-GAC GGG TTA GCG ACA AGC TCG-3' |
| F87V (SEQ ID NO: 10) | 5'-GAC GGG TTA GTG ACA AGC TGG-3' |
| E143G (SEQ ID NO: 11) | 5'-GAA GTA CCG GGC GAC ATG ACA-3' |
| L188Q (SEQ ID NO: 12) | 5'-ATG AAC AAG CAG CAG CGA GCA A-3' |
| A264G (SEQ ID NO: 13) | 5'-TTC TTA ATT GGG GGA CAC GTG-3' |
| E264G (SEQ ID NO: 14) | 5'-T GCG GGA CAC GTG ACA ACA AGT-3' |
| L86I/F87V (SEQ ID NO: 15) | 5'-GGA GAC GGG ATT GTG ACA AGC TG-3' |

EXAMPLE 2

Expression and Purification of Wild-Type CYP102A1 and Mutant Thereof

The plasmids including genes of the wild-type CYP102A1(pCWBM3) and the CYP102A1 mutants were transformed into *Escherichia coli* DH5α F'-IQ (Invitrogen) (see Kim et al., 2008). The culture was inoculated from a single colony into 5 ml of Luria-Bertani medium supplemented with ampicillin (100 μg/ml) and incubated at 37° C. After the culture, the obtained culture was inoculated into 250 ml of Terrific Broth medium supplemented with ampicillin (100 μg/ml), and was incubated at 37° C. with shaking at 250 rpm up to 0.8 at $OD_{600}$, and gene expression was induced by adding isopropyl-β-D-thiogalactopyranoside (IPTG) so as to have a final concentration of 0.5 mM, and δ-aminolevulinic acid (0.1 mM) was added thereto. After the expression was induced, the culture was further incubated at 30° C. for another 36 hours, and cells were harvested by centrifugation (15 minutes, 5,000 g, 4° C.). The cell pellet was obtained and re-suspended with TES buffer (100 mM Tris-HCl, pH 7.6, 500 mM sucrose, 0.5 mM EDTA), and the cells were lysed by sonication (sonicator; Misonix, Inc., Farmingdale, N.Y.). After the cell lysate was centrifuged under conditions of 100,000 g, 90 minutes and 4° C., soluble cytosolic fraction was collected to measure activity. The cytosolic fraction was dialyzed into a 50 mM potassium phosphate buffer (pH 7.4) and stored at −80° C., and the enzymes within 1 month after preparation were used for the experiment.

The concentration of CYP102A1 was determined by CO-difference spectrum, wherein ε is 91 mM/cm (Omura and Sato, 1964). In all of the wild-type CYP102A1 and the CYP102A1 mutants, the culture generally yielding 300 to 700 nM P450 could be generally obtained. An expression level of the wild-type CYP102A1 and the mutants thereof had a cytoplasmic protein range of 1.0 to 2.0 nmol P450/mg. Among the constructed mutants, the mutants having high catalytic activity to some substrates in human could be selected, and sites having the substitution of amino acids in each mutant were shown in Table 2.

TABLE 2

CYP102A1 mutants used in the present invention

| | | |
|---|---|---|
| Mutant #1 | F87A | Carmichael et al., 2001 |
| Mutant #2 | A264G | Carmichael et al., 2001 |
| Mutant #3 | F87A/A264G | Carmichael et al., 2001 |
| Mutant #4 | R47L/Y51F | Carmichael et al., 2001 |
| Mutant #5 | R47L/Y51F/A264G | Carmichael et al., 2001 |
| Mutant #6 | R47L/Y51F/F87A | Carmichael et al., 2001 |
| Mutant #7 | R47L/Y51F/F87A/A264G | Carmichael et al., 2001 |
| Mutant #8 | A74G/F87V/L188Q | Li et al., 2001 |
| Mutant #9 | R47L/L86I/L188Q | Kim et al., 2008a |
| Mutant #10 | R47L/F87V/L188Q | van Vugt Lusenburg et al., 2007 |
| Mutant #11 | R47L/F87V/L188Q/E267V | van Vugt Lusenburg et al., 2007 |
| Mutant #12 | R47L/L86I/L188Q/E267V | Kim et al., 2008 |
| Mutant #13 | R47L/L86I/F87V/L188Q | van Vugt Lusenburg et al., 2007 |
| Mutant #14 | R47L/F87V/E143G/L188Q/E267V | Kim et al., 2008a |
| Mutant #15 | R47L/E64G/F87V/E143G/L188Q/E267V | Kim et al., 2008a |
| Mutant #16 | R47L/F81I/F87V/E143G/L188Q/E267V | Kim et al., 2008a |
| Mutant #17 | R47L/E64G/F81I/F87V/E143G/L188Q/E267V | van Vugt Lusenburg et al., 2007 |

(Ref. Kim D. H., Kim K. H., Isin E. M., Guengerich F. P., Chae H. Z., Ahn T., and Yun C. H. (2008a) Heterologous Expression and Characterization of Wild-Type Human Cytochrome P450 1A2 Without Conventional N-Terminal Modification in *Escherichia Coli*. Protein Expr Purif. 57:188-200.)

EXAMPLE 3

Construction and Expression of CYP102A1 Chimera

Selective CYP102A1 chimera protein was constructed by fusing the heme domain of the CYP102A1 mutant shown in Table 2 with the reductase domain of the natural variant of the wild-type CYP102A1. Mutant#16 mutant was used as the CYP102A1 mutant, and natural mutants (Table 3) of *Bacillus megaterium* species were used as natural variants.

Figure 7:
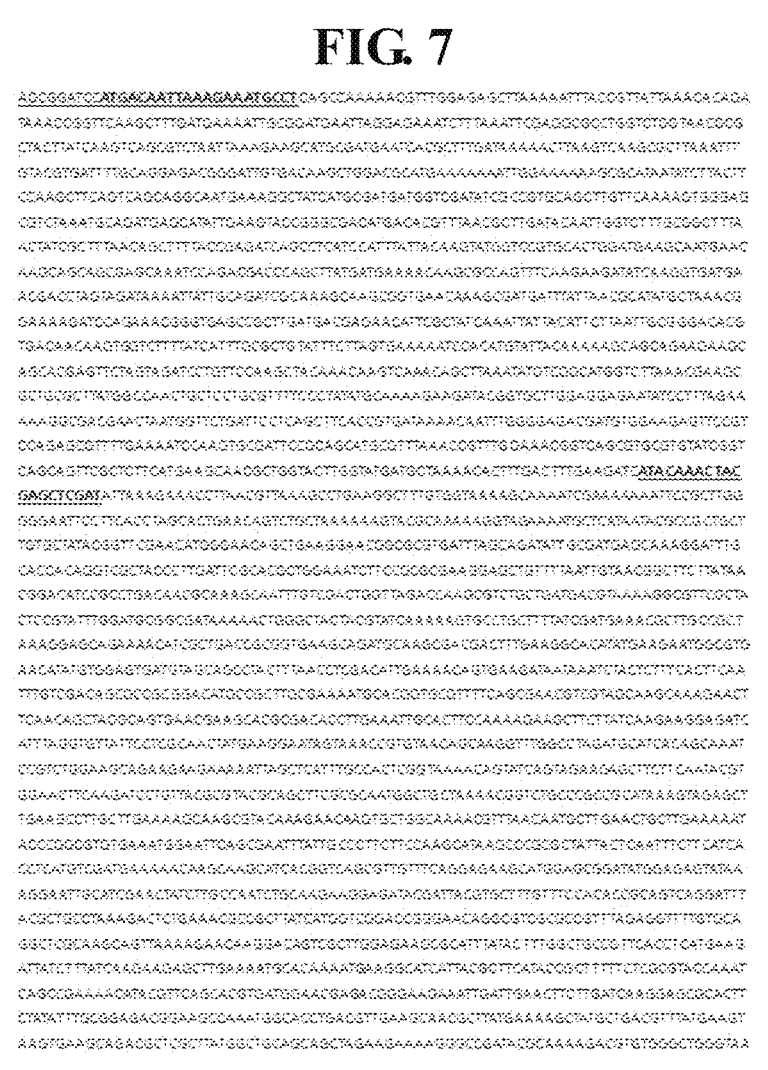

For the heme domain and the reductase domain, the CYP102A1 chimera constructed by using BamHI/SacI was cloned into the expression vector pCW vector. Specifically, gene segments including the Mutant#16 mutant were separated from the heme domain gene by treating each plasmid of the Mutant#16 mutant constructed by Examples 1 and 2 with BamHI/SacI restriction enzymes. M16V3 which is the chimera protein of the natural variant CYP102A1.3 and Mutant#16 including Mutant#16 mutant was produced by adding BamHI/SacI restriction enzyme to the plasmids of Mutant#16 mutant in DNA segments obtained by treating natural variants CYP102A1.3(KCCM 12503) with BamHI/SacI restriction enzyme. The nucleic acid and amino acid sequences of M16V3 were shown in FIGS. 7 and 8, respectively.

The plasmids including genes of CYP102A1 chimera were transformed into *Escherichia coli* DH5α F'-IQ (Invitrogen) (Kim et al., Protein Expr. Purif. 57:188-200, 2008). The culture was inoculated from a single colony into 5 ml of Luria-Bertani medium supplemented with ampicillin (100 μg/ml) and incubated at 37° C. After the culture, the obtained culture was inoculated into 250 ml of Terrific Broth medium supplemented with ampicillin (100 μg/ml), and incubated at 37° C. with shaking at 250 rpm up to 0.8 at $OD_{600}$, and gene expression was induced by adding isopropyl-β-D-thiogalactopyranoside (IPTG) so as to have a final concentration of 0.5 mM, and δ-aminolevulinic acid (0.1 mM) was added thereto. After the expression was induced, the culture was further incubated at 30° C. for another 36 hours, and cells were harvested by centrifugation (15 minutes, 5,000 g, 4° C.). The cell pellet was obtained and re-suspended with TES buffer (100 mM Tris-HCl, pH 7.6, 500 mM sucrose, 0.5 mM EDTA), and the cells were lysed by sonication (sonicator; Misonix, Inc., Farmingdale, N.Y.). After the cell lysate was centrifuged under conditions of 100,000 g, 90 minutes and 4° C., soluble cytosolic fraction was collected to measure activity. The cytosolic fraction was dialyzed into a 50 mM potassium phosphate buffer (pH 7.4) and stored at −80° C., and the enzymes within 1 month after preparation were used for the experiment.

The concentration of CYP102A1 chimera was determined by CO-difference spectrum, wherein ϵ is 91 mM/cm (Omura and Sato. J. Biol. Chem. 239:2379-2385, 1964).In the CYP102A1 chimera, the culture generally yielding 300 to 700 nM P450 could be obtained. The expression level of CYP102A1 chimera had a cytoplasmic protein range of 1.0 to 2.0 nmol P450/mg. Among the constructed CYP102A1 chimeras, the chimeras having high catalytic activity to some substrates in human could be selected, and sites having the substitution of amino acids in the CYP102A1 chimeras were shown in Table 4.

TABLE 3

Natural mutants used in the present invention

| | | Accession Number | | |
|---|---|---|---|---|
| Strain | Variant Name[b] | Genomic DNA | 16S rRNA | 16S-23S intergenic |
| KCCM 11745 | 102A1.1 | (J04832)[c] | FJ917385 | FJ969781 |
| IFO 12108 | 102A1.1 | (J04832)[c] | FJ969756 | FJ969774 |
| ATCC 14581 | 102A1.1 | (J04832)[c] | FJ969751 | FJ969767 |
| KCCM 41415 | 102A1.1 | (J04832)[c] | FJ969762 | FJ969792 |
| KCTC 3712 | 102A1.2 | FJ899078 | FJ969764 | FJ969795 |
| KCCM 12503 | 102A1.3 | FJ899082 | FJ969761 | FJ969787 |
| ATCC 15451 | 102A1.4 | FJ899085 | FJ969753 | FJ969768 |
| ATCC 10778 | 102A1.5 | FJ899078 | FJ969746 | FJ969765 |
| KCCM 11938 | 102A1.5 | FJ899078 | FJ969760 | FJ969786 |
| KCCM 11761 | 102A1.5 | FJ899078 | FJ969757 | FJ969783 |
| KCCM 11776 | 102A1.6 | FJ899081 | FJ969758 | FJ969784 |
| KCCM 11934 | 102A1.6 | FJ899081 | FJ969759 | FJ969785 |
| ATCC 14945 | 102A1.7 | FJ899084 | FJ969749 | FJ969766 |
| ATCC 21916 | 102A1.8 | FJ899092 | FJ969755 | FJ969772 |
| KCTC 2194 | 102A1.8 | FJ859036 | FJ969763 | FJ969794 |
| ATCC 19213 | 102A1.9 | FJ899091 | FJ969754 | FJ969769 |

TABLE 4

Chimera (M16V3) of CYP102A1 mutant used in the present invention

| Abbreviations | BM3 mutant | Ref |
|---|---|---|
| Variant3(V3) | A475V/E559D/T665A/P676L/A679E/ E688A/A742G/K814E/R826S/R837H/ E871N/I882V/E888G/P895S/S955N/ M968V/Q982R/A1009D/H1022Y/Q1023E | Kang et al. 2011 |

(Ref.: AMB Express 1(1):1. Kang J. Y.[1], Kim S. Y., Kim D., Kim D. H., Shin S. M., Park S. H., Kim K. H., Jung H. C., Pan J. G., Joung Y. H., Chi Y. T., Chae H. Z., Ahn T., Yun C. H. (2011) Characterization of Diverse Natural Variants of CYP102A1 Found Within A Species of *Bacillus Megaterium*)

EXAMPLE 4

Construction of Mutant of CYP102A1 Chimera by Site-Directed Mutagenesis

Three (3) different site-directed mutants of the CYP102A1 chimera were constructed by the same method as described in the research paper (see Generation of Human Metabolites of 7-Ethoxycoumarin by Bacterial Cytochrome P450 BM3. Drug Metabolism and Disposition 36(11):2166-2170. Page 2 (Page 2167), Materials and Methods, Construction of BM3 Mutants by Site-directed Mutagenesis, written by Kim D. H., Kim K. H., Kim D. H., Liu K. H., Jung H. C., Pan J. G., and Yun C. H. (2008)). Primers used for introducing BanHI/SacI recognition sites and PCR primers (XENOTECH, Korea) for inducing mutations were shown in Table 1. Codons for amino acid substitution were expressed in italics and underlines. The genes encoding the mutants of CYP102A1 chimera were amplified from pCWBM3 by PCR using primers designed for facilitating cloning into expression vector pCWori (obtained by Dr. F. W. Dahlquist, University of California, Santa Barbara, Calif.) or pSE420 (Invitrogen) (see Chimeric cytochromes P450 engineered by domain swapping and random mutagenesis for producing human metabolites of drugs. Biotechnology and Bioengineering 111(7):1313-1322, Page 1315, written by Kang J. Y., Ryu S. H., Park S. H., Cha G. S., Kim D. H., Kim K. H., Hong A. W., Ahn T., Pan J. G., Joung Y. H., Kang H. S., and Yun C. H. (2014)). Oligonucleotide assembly was performed by using the primers shown in Table 1. The amplified genes were cloned into the BamHI/SacI recognition site of pCWBM BamHI/SacI vector. The plasmids were transformed into *Escherichia coli* DH5α F'-IQ (Invitrogen) and were also used to express the mutant protein of CYP102A1 chimera. After mutagenesis, the presence of the desired mutations was confirmed by DNA sequencing (XENOTECH, Korea).

EXAMPLE 5

Expression and Purification of Mutant of CYP102A1 Chimera

The plasmids including the mutant gene of CYP102A1 chimera were transformed into *Escherichia coli* DH5α F'-IQ (Invitrogen). The culture was inoculated from a single colony into 5 ml of Luria-Bertani medium supplemented with ampicillin (100 μg/ml) and incubated at 37° C.

After the culture, the obtained culture was inoculated into 250 ml of Terrific Broth medium supplemented with ampicillin (100 µg/ml), and was incubated at 37° C. with shaking at 250 rpm up to 0.8 at $OD_{600}$, and gene expression was induced by adding isopropyl-β-D-thiogalactopyranoside (IPTG) so as to have a final concentration of 0.5 mM, and δ-aminolevulinic acid (0.1 mM) was added thereto. After the expression was induced, the culturing was additionally performed at 30° C. for another 36 hours, and centrifugation (15 minutes, 5,000 g, 4° C.) was performed, thereby harvesting cells. The cell pellet was obtained and re-suspended with TES buffer (100 mM Tris-HCl, pH 7.6, 500 mM sucrose, 0.5 mM EDTA), and the cells were lysed by sonication (sonicator; Misonix, Inc., Farmingdale, N.Y.). After the cell lysate was centrifuged under conditions of 100,000 g, 90 minutes and 4° C., soluble cytosolic fraction was collected to measure activity. The cytosolic fraction was dialyzed into a 50 mM potassium phosphate buffer (pH 7.4) and stored at −80° C., and the enzymes within 1 month after preparation were used for the experiment.

Mutants of CYP102A1 chimera concentration was determined by CO-difference spectrum, wherein ε is 91 mM/cm (Omura and Sato, 1964). In all of the wild-type CYP102A1 and the mutants of CYP102A1 chimera, the culture yielding 300 to 700 nM P450 could be generally obtained. An expression level of the wild-type CYP102A1 and the mutants of CYP102A1 chimera had a cytoplasmic protein range of 1.0 to 2.0 nmol P450/mg. Among the constructed mutants, the mutants having high catalytic activity to some substrates in human could be selected, and sites having the substitution of amino acids in each mutant were shown in Table 5.

TABLE 5

Mutants of CYP102A1 chimera used in the present invention

| Abbreviations | BM3 mutant |
|---|---|
| 387 | F11L/R47L/F81I/F87V/Q110P/E143G/L188Q/R190Q/E267V |
| 380 | R47L/F81I/F87V/L103F/D136G/E143G/N159S/L188Q/E267V |
| 306 | R47L/F81I/F87V/M112T/E143G/L188Q/E267V/M417T |

EXAMPLE 6

Confirmation of Oxidation of Polydatin

It was confirmed whether polydatin is oxidized in the wild-type CYP102A1, the CYP102A1 mutant, the CYP102A1 chimera, or the mutants of CYP102A1 chimera.

P450 BM3 50 pmol and 100 µl of polydatin as a substrate were added to 0.25 ml of 100 mM potassium phosphate buffer (pH 7.4) to perform a typical steady-state reaction. In order to start the reaction, the NADPH-generating system (10 mM glucose 6-phosphate, 0.5 mM $NADP^+$ and 1 IU yeast glucose 6-phosphate-dihydrogenase per 1 ml of final concentration) was added. 20 mM polydatin solution was prepared with DMSO, and diluted with an enzyme reaction solution, thereby preparing a reaction mixture so that the final organic solvent has a concentration of 1%/(v/v) or less. The solution was reacted at 37° C. for 30 minutes, and the reaction was terminated with ethyl-acetate which is cooled by ice with twice amount.

HPLC Analysis

The reaction mixture was centrifuged, the supernatant was removed and discarded. Then, the solvent was evaporated under a nitrogen gas, and analyzed by HPLC. A sample (30 µl) was injected into Gemini $C_{18}$ column (4.6 mm×150 mm, 5 µm, Phenomenex, Torrance, Calif.). As mobile phase, 85% A (acetonitrile/0.5%:acetic acid=5:95, v/v), 15% B (acetonitrile/0.5%:acetic acid=95:5) were used. The mobile phase flowed at a rate of 1 ml/minute and an eluent was measured by 320 nm of UV.

In order to examine whether polydatin is oxidized by CYP102A1(P450 BM3), oxidativity of polydatin was measured at a substrate concentration fixed to be 1000 µM in the P450 wild-type CYP102A1, the CYP102A1 mutant, the CYP102A1 chimera, and the mutant of CYP102A1 chimera.

FIG. 1 shows HPLC chromatogram of polydatin metabolites produced by the wild-type bacteria CYP102A1, the CYP102A1 mutant, the CYP102A1 chimera, and the mutant of CYP102A1 chimera. Referring to FIG. 1, the peak of new metabolites could be confirmed by comparing the peak with the NADPH-generating system with the peak without the NADPH-generating system. In addition, efficiency for producing the metabolites by selecting CYP102A1 chimera (M16V3) and three mutants (387, 380, 306) of CYP102A1 chimera were compared with each other by using kinetic parameter.

TABLE 6

Kinetic parameter of CYP102A1 chimera and mutants of CYP102A1 chimera

| | Astringin formation | | |
|---|---|---|---|
| CYP102A1 | $k_{cat}$ $min^{-1}$ | $K_m$ µM | $k_{cat}/K_m$ (relative catalytic efficiency) |
| M16V3 | 0.25 ± 0.03 | 390 ± 111 | 0.00064 (1) |
| 387 | 10.5 ± 0.4 | 475 ± 39 | 0.0221 (35) |
| 380 | 4.3 ± 0.5 | 481 ± 137 | 0.0089 (14) |
| 306 | 4.9 ± 0.8 | 398 ± 116 | 0.012 (19) |

LC-MS Analysis and NMR Analysis

In order to identify the metabolites of polydatin produced by the mutants of CYP102A1 chimera, LC-MS analysis was conducted by comparing polydatin and the metabolites according to LC profile and fragmentation patterns, and production of 3'-hydroxypolydatin (astringin) by the mutants of CYP102A1 chimera was confirmed by the LC-MS analysis of the reaction mixture including the mutant of CYP102A1 chimera.

The mutants of CYP102A1 chimera were reacted at 37° C. for 30 minutes in the presence of 1000 µM of polydatin and the NADPH-generating system. The reaction was terminated by adding twice amount of ethyl acetate which is cooled by ice. After centrifugation, the supernatant was removed and discarded, and the organic solvent layer was dried in the presence of nitrogen. The reactant was re-constituted into a vortex mixing with 100 µl of the mobile phase and was subjected to sonication for 20 seconds. An appropriate amount 5 µl of the prepared solution was injected into an LC column. The LC-MS analysis was conducted by Shimadzu LCMS-2010 EV system (Shimadzu, Kyoto, Japan) having an LC-MS software installed therein at an electro spray ionization(positive) mode. In the Shim-pack VP-ODS column (4.6 mm×150 mm i.d.; Shimadzu co., Japan), 85% A (acetonitrile/0.5%:acetic acid=5:95, v/v), 15% B (acetonitrile/0.5%:acetic acid=95:5) were used as mobile phases. The mobile phases were separated at a rate of 0.1 ml/min. In order to confirm the metabolite, mass spectra were recorded at an electro spray ionization (positive) mode. The interface and the detector volt were 4.4 kV and 1.5 kV, respectively. A nebulization gas rate was set to be 1.5 ml/min, and an interface, a curve desolvation line (CDL) and a heat-block temperature were set to be 250° C., 250° C. and 200° C., respectively.

Figure 2:
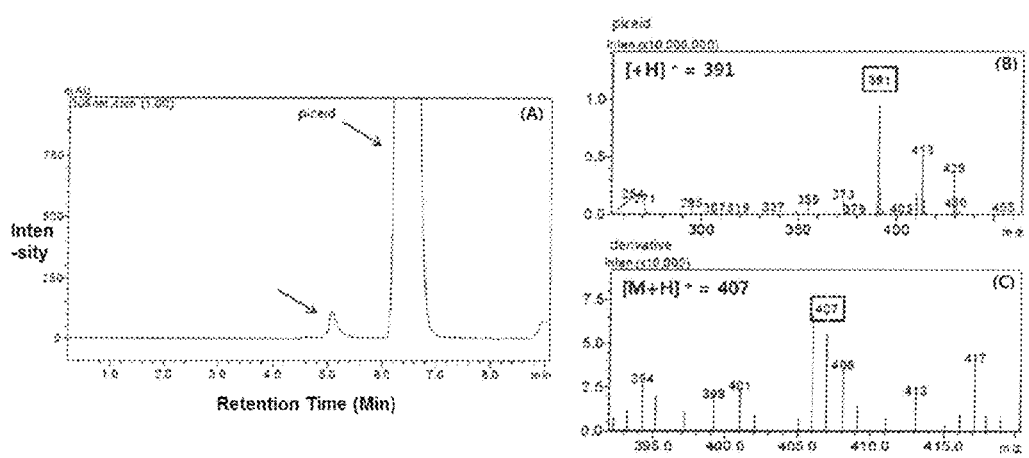
In FIG. 2, (A) shows LC-MS elution profiles of polydatin metabolites produced by the mutant 387 of bacteria CYP102A1 chimera, wherein peaks were shown at 5.182 min (3-hydroxypolydatin) and 6.453 min (polydatin) in the mass spectra. Further, the 3'-hydroxylated product and polydatin produced by mutant 387 of CYP102A1 chimera were observed at 391 (B) and 407 (C) ([M+H]$^+$) in mass spectra, respectively.
Figure 3:
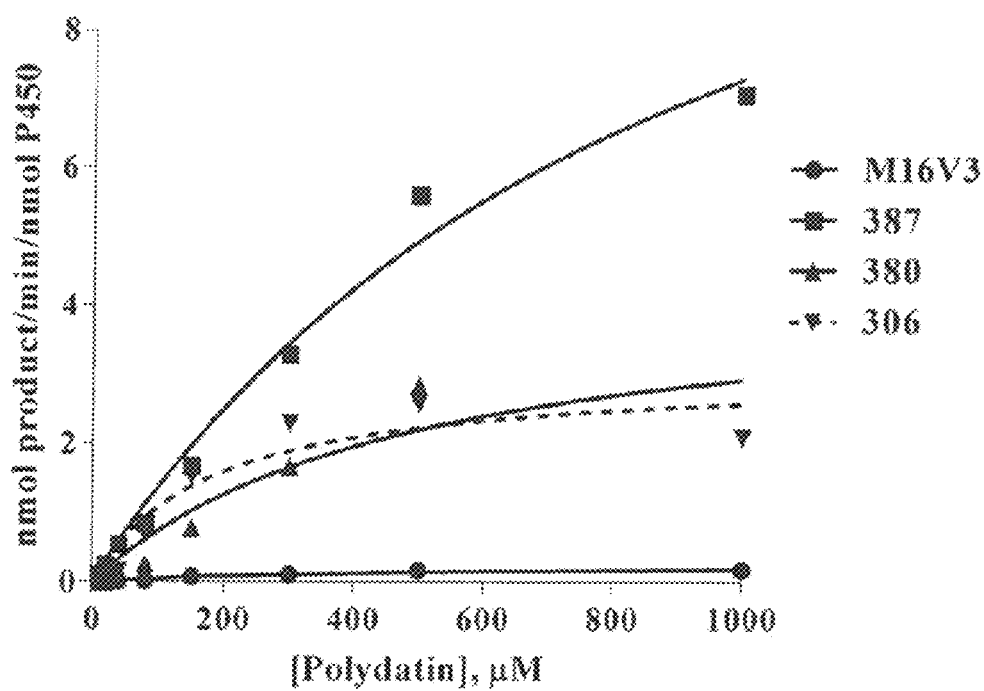
FIG. 3 shows analysis results of kinetic parameter by comparing production efficiency of 3'-hydroxylated products by bacteria CYP102A1 chimera (M16V3) and mutants (306, 380, 387) of CYP102A1 chimera.

FIG. 2 shows LC-MS elution profiles of polydatin and metabolites thereof, produced by the mutant 387 of CYP102A1 chimera. It shows total ion current (TIC) profile of the metabolites produced by the mutant 387 of CYP102A1 chimera. In the mass spectra of the reaction samples, peaks were shown at 5.182 min (3'-hydroxypolydatin), and 6.453 min (polydatin). 3'-hydroxypolydatin and polydatin produced by the mutant 387 of CYP102A1 chimera were observed at 407 and 391 ([M+H]$^+$) in mass spectra, respectively.

FIG. 4 shows the structures of the metabolites produced by the mutant 387 of the bacteria CYP102A1 chimera, and it was confirmed that the obtained product was astringin which is 3'-hydroxypoladatin by NMR analysis.

According to the present invention, astringin among metabolites of polydatin is capable of being produced from polydatin by using the composition including a cytochrome P450 chimeric enzyme and mutants thereof, which may be an alternative method to produce astringin in which the chemical synthesis has not yet been reported. In addition, astringin which is piceatannol glucoside among the metabolites of polydatin is capable of being specifically produced by using the composition including the cytochrome P450 chimeric enzyme and the mutants thereof, thereby having process benefits.

What is claimed is:

1. A composition for producing astringin from polydatin comprising a mutant of a CYP102A1 chimera,
   wherein the mutant of the CYP102A1 chimera is F11L/F81I/Q110P/R190Q of the CYP102A1 chimera, and
   wherein the CYP102A1 chimera consists of the amino acid sequence of SEQ ID NO: 18.

2. A kit for producing astringin from polydatin comprising a mutant of a CYP102A1 chimera and an NADPH-generating system,
   wherein the mutant of the CYP102A1 chimera is F11L/F81I/Q110P/R190Q of the CYP102A1 chimera; and
   wherein the CYP120A1 chimera consists of the amino acid sequence of SEQ ID NO: 18.

* * * * *

SEQUENCE LISTING

<160> NUMBER OF SEQ ID NOS: 19

<210> SEQ ID NO 1
<211> LENGTH: 31
<212> TYPE: DNA
<213> ORGANISM: Artificial Sequence
<220> FEATURE:
<223> OTHER INFORMATION: BamHI forward primer

<400> SEQUENCE: 1
agcggatcca tgacaattaa agaaatgcct c        31

<210> SEQ ID NO 2
<211> LENGTH: 20
<212> TYPE: DNA
<213> ORGANISM: Artificial Sequence
<220> FEATURE:
<223> OTHER INFORMATION: SacI reverse primer

<400> SEQUENCE: 2
atcgagctcg tagtttgtat        20

<210> SEQ ID NO 3
<211> LENGTH: 20
<212> TYPE: DNA
<213> ORGANISM: Artificial Sequence
<220> FEATURE:
<223> OTHER INFORMATION: R47L primer

<400> SEQUENCE: 3
gcgcctggtc tggtaacgcg        20

<210> SEQ ID NO 4
<211> LENGTH: 21
<212> TYPE: DNA
<213> ORGANISM: Artificial Sequence
<220> FEATURE:
<223> OTHER INFORMATION: Y51F primer

<400> SEQUENCE: 4
gtaacgcgct tcttatcaag t        21

<210> SEQ ID NO 5
<211> LENGTH: 21
<212> TYPE: DNA
<213> ORGANISM: Artificial Sequence
<220> FEATURE:
<223> OTHER INFORMATION: E64G primer

<400> SEQUENCE: 5
gcatgcgatg gctcacgctt t          21

<210> SEQ ID NO 6
<211> LENGTH: 25
<212> TYPE: DNA
<213> ORGANISM: Artificial Sequence
<220> FEATURE:
<223> OTHER INFORMATION: A74G primer

<400> SEQUENCE: 6
taagtcaagg ccttaaattt gtacg          25

<210> SEQ ID NO 7
<211> LENGTH: 21
<212> TYPE: DNA
<213> ORGANISM: Artificial Sequence
<220> FEATURE:
<223> OTHER INFORMATION: F81I primer

<400> SEQUENCE: 7
gtacgtgata ttgcaggaga c          21

<210> SEQ ID NO 8
<211> LENGTH: 22
<212> TYPE: DNA
<213> ORGANISM: Artificial Sequence
<220> FEATURE:
<223> OTHER INFORMATION: L86I primer

<400> SEQUENCE: 8
ggagacggga tttttacaag ct          22

<210> SEQ ID NO 9
<211> LENGTH: 21
<212> TYPE: DNA
<213> ORGANISM: Artificial Sequence
<220> FEATURE:
<223> OTHER INFORMATION: F87A primer

<400> SEQUENCE: 9
gacgggttag cgacaagctg g          21

<210> SEQ ID NO 10
<211> LENGTH: 21
<212> TYPE: DNA
<213> ORGANISM: Artificial Sequence
<220> FEATURE:
<223> OTHER INFORMATION: F87V primer

<400> SEQUENCE: 10
gacgggttag tgacaagctg g          21

<210> SEQ ID NO 11
<211> LENGTH: 21
<212> TYPE: DNA
<213> ORGANISM: Artificial Sequence
<220> FEATURE:
<223> OTHER INFORMATION: E143G primer

<400> SEQUENCE: 11
gaagtaccgg gcgacatgac a          21

<210> SEQ ID NO 12
<211> LENGTH: 22
<212> TYPE: DNA
<213> ORGANISM: Artificial Sequence
<220> FEATURE:
<223> OTHER INFORMATION: L188Q primer

<400> SEQUENCE: 12
atgaacaagc agcagcgagc aa                                              22

<210> SEQ ID NO 13
<211> LENGTH: 21
<212> TYPE: DNA
<213> ORGANISM: Artificial Sequence
<220> FEATURE:
<223> OTHER INFORMATION: A264G primer

<400> SEQUENCE: 13
ttcttaattg ggggacacgt g                                               21

<210> SEQ ID NO 14
<211> LENGTH: 22
<212> TYPE: DNA
<213> ORGANISM: Artificial Sequence
<220> FEATURE:
<223> OTHER INFORMATION: E267V primer

<400> SEQUENCE: 14
tgcgggacac gtgacaacaa gt                                              22

<210> SEQ ID NO 15
<211> LENGTH: 23
<212> TYPE: DNA
<213> ORGANISM: Artificial Sequence
<220> FEATURE:
<223> OTHER INFORMATION: L86I/F87V primer

<400> SEQUENCE: 15
ggagacggga ttgtgacaag ctg                                             23

<210> SEQ ID NO 16
<211> LENGTH: 1048
<212> TYPE: PRT
<213> ORGANISM: Artificial Sequence
<220> FEATURE:
<223> OTHER INFORMATION: wild type CYP102A1

<400> SEQUENCE: 16

Thr Ile Lys Glu Met Pro Gln Pro Lys Thr Phe Gly Glu Leu Lys Asn
 1               5                  10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Phe Val Arg Asp
65                  70                  75                  80

Phe Ala Gly Asp Gly Leu Phe Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Pro Glu Asp
    130                 135                 140

-continued

```
Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
            165                 170                 175

Met Val Arg Ala Leu Asp Glu Ala Met Asn Lys Leu Gln Arg Ala Asn
        180                 185                 190

Pro Asp Asp Pro Ala Tyr Glu Asp Asn Lys Arg Gln Phe Gln Glu Lys
    195                 200                 205

Ile Lys Val Met Asn Asp Leu Val Asp Lys Ile Ile Ala Lys Arg Lys
210                 215                 220

Ala Ser Gly Glu Gln Ser Asp Asp Leu Leu Thr His Met Leu Asn Gly
225                 230                 235                 240

Lys Asp Pro Glu Thr Gly Glu Pro Leu Asp Asp Glu Asn Ile Arg Tyr
            245                 250                 255

Gln Ile Ile Thr Phe Leu Ile Ala Gly His Glu Thr Thr Ser Gly Leu
        260                 265                 270

Leu Ser Phe Ala Leu Tyr Phe Leu Val Lys Asn Pro His Val Leu Gln
    275                 280                 285

Lys Ala Ala Glu Glu Ala Ala Arg Val Leu Val Asp Pro Val Pro Ser
290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Leu Ser Tyr Ala Lys
            325                 330                 335

Glu Asp Thr Val Leu Gly Gly Glu Tyr Pro Leu Glu Lys Gly Asp Glu
        340                 345                 350

Leu Met Val Leu Ile Pro Gln Leu His Arg Asp Lys Thr Ile Trp Gly
    355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
            405                 410                 415

Met Leu Lys His Phe Asp Phe Glu Asp His Thr Asn Tyr Glu Leu Asp
        420                 425                 430

Ile Lys Glu Thr Leu Thr Leu Lys Pro Glu Gly Phe Val Val Lys Ala
    435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
            485                 490                 495

Ala Arg Asp Leu Ala Asp Ile Ala Met Ser Lys Gly Phe Ala Pro Gln
        500                 505                 510

Val Ala Thr Leu Asp Ser His Ala Gly Asn Leu Pro Arg Glu Gly Ala
    515                 520                 525

Val Leu Ile Val Thr Ala Ser Tyr Asn Gly His Pro Pro Lys Asn Ala
530                 535                 540

Lys Gln Phe Val Asp Trp Leu Asp Gln Ala Ser Ala Asp Glu Val Lys
545                 550                 555                 560
```

-continued

Gly Val Arg Tyr Ser Val Phe Gly Cys Gly Asp Lys Asn Trp Ala Thr
            565                 570                 575

Thr Tyr Gln Lys Val Pro Ala Phe Ile Asp Glu Thr Leu Ala Ala Lys
        580                 585                 590

Gly Ala Glu Asn Ile Ala Asp Arg Gly Glu Ala Asp Ala Ser Asp Asp
    595                 600                 605

Phe Glu Gly Thr Tyr Glu Glu Trp Arg Glu His Met Trp Ser Asp Val
610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
            645                 650                 655

Lys Met His Gly Ala Phe Ser Thr Asn Val Val Ala Ser Lys Glu Leu
        660                 665                 670

Gln Gln Pro Gly Ser Ala Arg Ser Thr Arg His Leu Glu Ile Glu Leu
    675                 680                 685

Pro Lys Glu Ala Ser Tyr Gln Glu Gly Asp His Leu Gly Val Ile Pro
690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
            725                 730                 735

His Leu Pro Leu Ala Lys Thr Val Ser Val Glu Glu Leu Leu Gln Tyr
        740                 745                 750

Val Glu Leu Gln Asp Pro Val Thr Arg Thr Gln Leu Arg Ala Met Ala
    755                 760                 765

Ala Lys Thr Val Cys Pro Pro His Lys Val Glu Leu Glu Ala Leu Leu
770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
            805                 810                 815

Phe Ile Ala Leu Leu Pro Ser Ile Arg Pro Arg Tyr Tyr Ser Ile Ser
        820                 825                 830

Ser Ser Pro Arg Val Asp Glu Lys Gln Ala Ser Ile Thr Val Ser Val
    835                 840                 845

Val Ser Gly Glu Ala Trp Ser Gly Tyr Gly Glu Tyr Lys Gly Ile Ala
850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
            885                 890                 895

Pro Leu Ile Met Val Gly Pro Gly Thr Gly Val Ala Pro Phe Arg Gly
        900                 905                 910

Phe Val Gln Ala Arg Lys Gln Leu Lys Glu Gln Gly Gln Leu Ser Gly
    915                 920                 925

Glu Ala His Leu Tyr Phe Gly Cys Arg Ser Pro His Glu Asp Tyr Leu
930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
            965                 970                 975

His Val Met Glu Gln Asp Gly Lys Lys Leu Ile Glu Leu Leu Asp Gln

-continued

```
            980             985             990
Gly Ala His Phe Tyr Ile Cys Gly Asp Gly Ser Gln Met Ala Pro Ala
                995             1000            1005

Val Glu Ala Thr Leu Met Lys Ser Tyr Ala Asp Val His Gln Val Ser
    1010            1015            1020

Glu Ala Asp Ala Arg Leu Trp Leu Gln Gln Leu Glu Glu Lys Gly Arg
1025            1030            1035            1040

Tyr Ala Lys Asp Val Trp Ala Gly
            1045

<210> SEQ ID NO 17
<211> LENGTH: 3159
<212> TYPE: DNA
<213> ORGANISM: Artificial Sequence
<220> FEATURE:
<223> OTHER INFORMATION: CYP102A1 chimeric protein M16V3

<400> SEQUENCE: 17
```

| | | | | | |
|---|---|---|---|---|---|
| agcggatcca | tgacaattaa | agaaatgcct | cagccaaaaa | cgtttggaga | gcttaaaaat | 60 |
| ttaccgttat | taaacacaga | taaaccggtt | caagctttga | tgaaaattgc | ggatgaatta | 120 |
| ggagaaatct | ttaaattcga | ggcgcctggt | ctggtaacgc | gctacttatc | aagtcagcgt | 180 |
| ctaattaaag | aagcatgcga | tgaatcacgc | tttgataaaa | acttaagtca | agcgcttaaa | 240 |
| tttgtacgtg | attttgcagg | agacgggatt | gtgacaagct | ggacgcatga | aaaaaattgg | 300 |
| aaaaaagcgc | ataatatctt | acttccaagc | ttcagtcagc | aggcaatgaa | aggctatcat | 360 |
| gcgatgatgg | tcgatatcgc | cgtgcagctt | gttcaaaagt | gggagcgtct | aaatgcagat | 420 |
| gagcatattg | aagtaccggg | cgacatgaca | cgtttaacgc | ttgatacaat | tggtctttgc | 480 |
| ggctttaact | atcgctttaa | cagcttttac | cgagatcagc | ctcatccatt | tattacaagt | 540 |
| atggtccgtg | cactggatga | agcaatgaac | aagcagcagc | gagcaaatcc | agacgaccca | 600 |
| gcttatgatg | aaaacaagcg | ccagtttcaa | gaagatatca | aggtgatgaa | cgacctagta | 660 |
| gataaaatta | ttgcagatcg | caaagcaagc | ggtgaacaaa | gcgatgattt | attaacgcat | 720 |
| atgctaaacg | gaaagatcc | agaaacgggt | gagccgcttg | atgacgagaa | cattcgctat | 780 |
| caaattatta | cattcttaat | tgcgggacac | gtgacaacaa | gtggtctttt | atcatttgcg | 840 |
| ctgtatttct | tagtgaaaaa | tccacatgta | ttacaaaaag | cagcagaaga | agcagcacga | 900 |
| gttctagtag | atcctgttcc | aagctacaaa | caagtcaaac | agcttaaata | tgtcggcatg | 960 |
| gtcttaaacg | aagcgctgcg | cttatggcca | actgctcctg | cgttttccct | atatgcaaaa | 1020 |
| gaagatacgg | tgcttggagg | agaatatcct | ttagaaaaag | gcgacgaact | aatggttctg | 1080 |
| attcctcagc | ttcaccgtga | taaaacaatt | tggggagacg | atgtggaaga | gttccgtcca | 1140 |
| gagcgttttg | aaaatccaag | tgcgattccg | cagcatgcgt | ttaaaccgtt | tggaaacggt | 1200 |
| cagcgtgcgt | gtatcggtca | gcagttcgct | cttcatgaag | caacgctggt | acttggtatg | 1260 |
| atgctaaaac | actttgactt | tgaagatcat | acaaactacg | agctcgatat | taagaaaacc | 1320 |
| ttaacgttaa | agcctgaagg | ctttgtggta | aaagcaaaat | cgaaaaaaat | tccgcttggg | 1380 |
| ggaattcctt | cacctagcac | tgaacagtct | gctaaaaaag | tacgcaaaaa | ggtagaaaat | 1440 |
| gctcataata | cgccgctgct | tgtgctatac | ggttcgaaca | tgggaacagc | tgaaggaacg | 1500 |
| gcgcgtgatt | tagcagatat | tgcgatgagc | aaaggatttg | caccacaggt | cgctaccctt | 1560 |
| gattcgcacg | ctgaaatctc | tccgcgcgaa | ggagctgttt | taattgtaac | ggcttcttat | 1620 |
| aacggacatc | cgcctgacaa | cgcaaagcaa | tttgtcgact | ggttagacca | agcgtctgct | 1680 |

```
gatgacgtaa aaggcgttcg ctactccgta tttggatgcg gcgataaaaa ctgggctact    1740
acgtatcaaa aagtgcctgc ttttatcgat gaaacgcttg ccgctaaagg agcagaaaac    1800
atcgctgacc gcggtgaagc agatgcaagc gacgactttg aaggcacata tgaagaatgg    1860
cgtgaacata tgtggagtga tgtagcagcc tactttaacc tcgacattga aaacagtgaa    1920
gataataaat ctactctttc acttcaattt gtcgacagcg ccgcggacat gccgcttgcg    1980
aaaatgcacg gtgcgttttc agcgaacgtc gtagcaagca aagaacttca acagctaggc    2040
agtgaacgaa gcacgcgaca ccttgaaatt gcacttccaa agaagcttc ttatcaagaa     2100 ggagatcatt taggtgttat tcctcgcaac tatgaaggaa tagtaaaccg tgtaacagca    2160
aggtttggcc tagatgcatc acagcaaatc cgtctggaag cagaagaaga aaaattagct    2220
catttgccac tcggtaaaac agtatcagta gaagagcttc ttcaatacgt ggaacttcaa    2280
gatcctgtta cgcgtacgca gcttcgcgca atggctgcta aaacggtctg cccgccgcat    2340
aaagtagagc ttgaagcctt gcttgaaaag caagcgtaca agaacaagt gctggcaaaa     2400 cgtttaacaa tgcttgaact gcttgaaaaa tacccggcgt gtgaaatgga attcagcgaa    2460
tttattgccc ttcttccaag cataagcccg cgctattact caatttcttc atcacctcat    2520
gtcgatgaaa acaagcaag catcacggtc agcgttgttt caggagaagc atggagcgga    2580
tatggagagt ataaaggaat tgcatcgaac tatcttgcca atctgcaaga aggagatacg    2640
attacgtgct ttgtttccac accgcagtca ggatttacgc tgcctaaaga ctctgaaacg    2700
ccgcttatca tggtcggacc gggaacaggc gtcgcgccgt ttagaggttt tgtgcaggct    2760
cgcaagcagt taaaagaaca aggacagtcg cttggagaag cgcatttata ctttggctgc    2820
cgttcacctc atgaagatta tctttatcaa gaagagcttg aaaatgcaca aaatgaaggc    2880
atcattacgc ttcataccgc ttttttctcgc gtaccaaatc agccgaaaac atacgttcag    2940
cacgtgatgg aacgagacgg gaagaaattg attgaacttc ttgatcaagg agcgcacttc    3000
tatatttgcg gagacggaag ccaaatggca cctgacgttg aagcaacgct tatgaaaagc    3060
tatgctgacg tttatgaagt aagtgaagca gacgctcgct tatggctgca gcagctagaa    3120
gaaaagggcc gatacgcaaa agacgtgtgg gctgggtaa                          3159

<210> SEQ ID NO 18
<211> LENGTH: 1048
<212> TYPE: PRT
<213> ORGANISM: Artificial Sequence
<220> FEATURE:
<223> OTHER INFORMATION: CYP102A1 chimeric protein M16V3 aa seq

<400> SEQUENCE: 18

Thr Ile Lys Glu Met Pro Gln Pro Lys Thr Phe Gly Glu Leu Lys Asn
  1               5                  10                  15

Leu Pro Leu Leu Asn Thr Asp Lys Pro Val Gln Ala Leu Met Lys Ile
             20                  25                  30

Ala Asp Glu Leu Gly Glu Ile Phe Lys Phe Glu Ala Pro Gly Leu Val
         35                  40                  45

Thr Arg Tyr Leu Ser Ser Gln Arg Leu Ile Lys Glu Ala Cys Asp Glu
     50                  55                  60

Ser Arg Phe Asp Lys Asn Leu Ser Gln Ala Leu Lys Phe Val Arg Asp
 65                  70                  75                  80

Phe Ala Gly Asp Gly Ile Val Thr Ser Trp Thr His Glu Lys Asn Trp
                 85                  90                  95
```

-continued

Lys Lys Ala His Asn Ile Leu Leu Pro Ser Phe Ser Gln Gln Ala Met
                100                 105                 110

Lys Gly Tyr His Ala Met Met Val Asp Ile Ala Val Gln Leu Val Gln
            115                 120                 125

Lys Trp Glu Arg Leu Asn Ala Asp Glu His Ile Glu Val Pro Gly Asp
        130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
                165                 170                 175

Met Val Arg Ala Leu Asp Glu Ala Met Asn Lys Gln Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Lys Ile Ile Ala Asp Arg Lys
210                 215                 220

Ala Ser Gly Glu Gln Ser Asp Asp Leu Leu Thr His Met Leu Asn Gly
225                 230                 235                 240

Lys Asp Pro Glu Thr Gly Glu Pro Leu Asp Asp Glu Asn Ile Arg Tyr
                245                 250                 255

Gln Ile Ile Thr Phe Leu Ile Ala Gly His Val Thr Thr Ser Gly Leu
            260                 265                 270

Leu Ser Phe Ala Leu Tyr Phe Leu Val Lys Asn Pro His Val Leu Gln
        275                 280                 285

Lys Ala Ala Glu Glu Ala Ala Arg Val Leu Val Asp Pro Val Pro Ser
290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Leu Met Val Leu Ile Pro Gln Leu His Arg Asp Lys Thr Ile Trp Gly
        355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
        435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Val Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala

-continued

```
            515                 520                 525
Val Leu Ile Val Thr Ala Ser Tyr Asn Gly His Pro Pro Asp Asn Ala
        530                 535                 540
Lys Gln Phe Val Asp Trp Leu Asp Gln Ala Ser Ala Asp Asp Val Lys
545                 550                 555                 560
Gly Val Arg Tyr Ser Val Phe Gly Cys Gly Asp Lys Asn Trp Ala Thr
                565                 570                 575
Thr Tyr Gln Lys Val Pro Ala Phe Ile Asp Glu Thr Leu Ala Ala Lys
            580                 585                 590
Gly Ala Glu Asn Ile Ala Asp Arg Gly Glu Ala Asp Ala Ser Asp Asp
            595                 600                 605
Phe Glu Gly Thr Tyr Glu Glu Trp Arg Glu His Met Trp Ser Asp Val
        610                 615                 620
Ala Ala Tyr Phe Asn Leu Asp Ile Glu Asn Ser Glu Asp Asn Lys Ser
625                 630                 635                 640
Thr Leu Ser Leu Gln Phe Val Asp Ser Ala Ala Asp Met Pro Leu Ala
                645                 650                 655
Lys Met His Gly Ala Phe Ser Ala Asn Val Val Ala Ser Lys Glu Leu
            660                 665                 670
Gln Gln Leu Gly Ser Glu Arg Ser Thr Arg His Leu Glu Ile Ala Leu
        675                 680                 685
Pro Lys Glu Ala Ser Tyr Gln Glu Gly Asp His Leu Gly Val Ile Pro
690                 695                 700
Arg Asn Tyr Glu Gly Ile Val Asn Arg Val Thr Ala Arg Phe Gly Leu
705                 710                 715                 720
Asp Ala Ser Gln Gln Ile Arg Leu Glu Ala Glu Glu Lys Leu Ala
                725                 730                 735
His Leu Pro Leu Gly Lys Thr Val Ser Val Glu Leu Leu Gln Tyr
            740                 745                 750
Val Glu Leu Gln Asp Pro Val Thr Arg Thr Gln Leu Arg Ala Met Ala
        755                 760                 765
Ala Lys Thr Val Cys Pro Pro His Lys Val Glu Leu Glu Ala Leu Leu
        770                 775                 780
Glu Lys Gln Ala Tyr Lys Glu Gln Val Leu Ala Lys Arg Leu Thr Met
785                 790                 795                 800
Leu Glu Leu Leu Glu Lys Tyr Pro Ala Cys Glu Met Glu Phe Ser Glu
                805                 810                 815
Phe Ile Ala Leu Leu Pro Ser Ile Ser Pro Arg Tyr Tyr Ser Ile Ser
            820                 825                 830
Ser Ser Pro His Val Asp Glu Lys Gln Ala Ser Ile Thr Val Ser Val
        835                 840                 845
Val Ser Gly Glu Ala Trp Ser Gly Tyr Gly Glu Tyr Lys Gly Ile Ala
        850                 855                 860
Ser Asn Tyr Leu Ala Asn Leu Gln Glu Gly Asp Thr Ile Thr Cys Phe
865                 870                 875                 880
Val Ser Thr Pro Gln Ser Gly Phe Thr Leu Pro Lys Asp Ser Glu Thr
                885                 890                 895
Pro Leu Ile Met Val Gly Pro Gly Thr Gly Val Ala Pro Phe Arg Gly
            900                 905                 910
Phe Val Gln Ala Arg Lys Gln Leu Lys Glu Gln Gly Gln Ser Leu Gly
        915                 920                 925
Glu Ala His Leu Tyr Phe Gly Cys Arg Ser Pro His Glu Asp Tyr Leu
        930                 935                 940
```

Tyr Gln Glu Glu Leu Glu Asn Ala Gln Asn Glu Gly Ile Ile Thr Leu
945                 950                 955                 960

His Thr Ala Phe Ser Arg Val Pro Asn Gln Pro Lys Thr Tyr Val Gln
            965                 970                 975

His Val Met Glu Arg Asp Gly Lys Lys Leu Ile Glu Leu Leu Asp Gln
        980                 985                 990

Gly Ala His Phe Tyr Ile Cys Gly Asp Gly Ser Gln Met Ala Pro Asp
        995                 1000                1005

Val Glu Ala Thr Leu Met Lys Ser Tyr Ala Asp Val Tyr Glu Val Ser
    1010                1015                1020

Glu Ala Asp Ala Arg Leu Trp Leu Gln Gln Leu Glu Glu Lys Gly Arg
1025                1030                1035                1040

Tyr Ala Lys Asp Val Trp Ala Gly
            1045

<210> SEQ ID NO 19
<211> LENGTH: 3150
<212> TYPE: DNA
<213> ORGANISM: Artificial Sequence
<220> FEATURE:
<223> OTHER INFORMATION: CYP102A1 Mutant#16

<400> SEQUENCE: 19

| | | | | | |
|---|---|---|---|---|---|
| atgacaatta | aagaaatgcc | tcagccaaaa | acgtttggag | agcttaaaaa | tttaccgtta | 60 |
| ttaaacacag | ataaaccggt | tcaagctttg | atgaaaattg | cggatgaatt | aggagaaatc | 120 |
| tttaaattcg | aggcgcctgg | tcttgtaacg | cgctacttat | caagtcagcg | tctaattaaa | 180 |
| gaagcatgcg | atgaatcacg | ctttgataaa | aacttaagtc | aagcgcttaa | atttgtacgt | 240 |
| gatattgcag | agacgggtt | agttacaagc | tggacgcatg | aaaaaaattg | gaaaaaagcg | 300 |
| cataatatct | tacttccaag | cttcagtcag | caggcaatga | aaggctatca | tgcgatgatg | 360 |
| gtcgatatcg | ccgtgcagct | tgttcaaaag | tgggagcgtc | taaatgcaga | tgagcatatt | 420 |
| gaagtaccgg | agacatgac | acgtttaacg | cttgatacaa | ttggtctttg | cggctttaac | 480 |
| tatcgcttta | acagctttta | ccgagatcag | cctcatccat | ttattacaag | tatggtccgt | 540 |
| gcactggatg | aagcaatgaa | caagcagcag | cgagcaaatc | cagacgaccc | agcttatgat | 600 |
| gaaaacaagc | gccagtttca | agaagatatc | aaggtgatga | cgacctagt | agataaaatt | 660 |
| attgcagatc | gcaaagcaag | cggtgaacaa | agcgatgatt | tattaacgca | tatgctaaac | 720 |
| ggaaaagatc | cagaaacggg | tgagccgctt | gatgacgaga | cattcgcta | tcaaattatt | 780 |
| acattcttaa | ttgcgggaca | cgtaacaaca | agtggtcttt | tatcatttgc | gctgtatttc | 840 |
| ttagtgaaaa | atccacatgt | attacaaaaa | gcagcagaag | aagcagcacg | agttctagta | 900 |
| gatcctgttc | caagctacaa | acaagtcaaa | cagcttaaat | atgtcggcat | ggtcttaaac | 960 |
| gaagcgctgc | gcttatggcc | aactgctcct | gcgttttccc | tatatgcaaa | agaagatacg | 1020 |
| gtgcttggag | gagaatatcc | tttagaaaaa | ggcgacgaac | taatggttct | gattcctcag | 1080 |
| cttcaccgtg | ataaaacaat | ttggggagac | gatgtggaag | agttccgtcc | agagcgtttt | 1140 |
| gaaaatccaa | gtgcgattcc | gcagcatgcg | tttaaaccgt | tggaaacgg | tcagcgtgcg | 1200 |
| tgtatcggtc | agcagttcgc | tcttcatgaa | gcaacgctgg | tacttggtat | gatgctaaaa | 1260 |
| cactttgact | ttgaagatca | tacaaactac | gagctcgata | ttaagaaac | tttaacgtta | 1320 |
| aaacctgaag | gctttgtggt | aaaagcaaaa | tcgaaaaaa | ttccgcttgg | cggtattcct | 1380 |
| tcacctagca | ctgaacagtc | tgctaaaaaa | gtacgcaaaa | aggcagaaaa | cgctcataat | 1440 |

```
acgccgctgc ttgtgctata cggttcaaat atgggaacag ctgaaggaac ggcgcgtgat   1500
ttagcagata ttgcaatgag caaaggattt gcaccgcagg tcgcaacgct tgattcacac   1560
gccggaaatc ttccgcgcga aggagctgta ttaattgtaa cggcgtctta taacggtcat   1620
ccgcctgata acgcaaagca atttgtcgac tggttagacc aagcgtctgc tgatgaagta   1680
aaaggcgttc gctactccgt atttggatgc ggcgataaaa actgggctac tacgtatcaa   1740
aaagtgcctg cttttatcga tgaaacgctt gccgctaaag gggcagaaaa catcgctgac   1800
cgcggtgaag cagatgcaag cgacgacttt gaaggcacat atgaagaatg cgtgaacat   1860 atgtggagtg acgtagcagc ctactttaac ctcgacattg aaaacagtga agataataaa   1920
tctactcttt cacttcaatt tgtcgacagc gccgcggata tgccgcttgc gaaaatgcac   1980
ggtgcgtttt caacgaacgt cgtagcaagc aaagaacttc aacagccagg cagtgcacga   2040
agcacgcgac atcttgaaat tgaacttcca aaagaagctt cttatcaaga aggagatcat   2100
ttaggtgtta ttcctcgcaa ctatgaagga atagtaaacc gtgtaacagc aaggttcggc   2160
ctagatgcat cacagcaaat ccgtctggaa gcagaagaag aaaaattagc tcatttgcca   2220
ctcgctaaaa cagtatccgt agaagagctt ctgcaatacg tggagcttca agatcctgtt   2280
acgcgcacgc agcttcgcgc aatggctgct aaaacggtct gcccgccgca taagtagag   2340 cttgaagcct tgcttgaaaa gcaagcctac aaagaacaag tgctggcaaa acgtttaaca   2400
atgcttgaac tgcttgaaaa atacccggcg tgtgaaatga aattcagcga atttatcgcc   2460
cttctgccaa gcatacgccc gcgctattac tcgatttctt catcacctcg tgtcgatgaa   2520
aaacaagcaa gcatcacggt cagcgttgtc tcaggagaag cgtggagcgg atatggagaa   2580
tataaaggaa ttgcgtcgaa ctatcttgcc gagctgcaag aaggagatac gattacgtgc   2640
tttatttcca caccgcagtc agaatttacg ctgccaaaag accctgaaac gccgcttatc   2700
atggtcggac cgggaacagg cgtcgcgccg tttagaggct ttgtgcaggc gcgcaaacag   2760
ctaaaagaac aaggacagtc acttggagaa gcacatttat acttcggctg ccgttcacct   2820
catgaagact atctgtatca agaagagctt gaaaacgccc aaagcgaagg catcattacg   2880
cttcataccg cttttctcg catgccaaat cagccgaaaa catacgttca gcacgtaatg   2940
gaacaagacg gcaagaaatt gattgaactt cttgatcaag gagcgcactt ctatatttgc   3000
ggagacggaa gccaaatggc acctgccgtt gaagcaacgc ttatgaaaag ctatgctgac   3060
gttcaccaag tgagtgaagc agacgctcgc ttatggctgc agcagctaga agaaaaaggc   3120
cgatacgcaa aagacgtgtg ggctgggtaa                                     3150
```